United States Patent
Mendes

(10) Patent No.: US 11,768,199 B2
(45) Date of Patent: Sep. 26, 2023

(54) STIMULI-RESPONSIVE SURFACES

(71) Applicant: The University of Birmingham, Birmingham (GB)

(72) Inventor: Paula Mendes, Birmingham (GB)

(73) Assignee: The University of Birmingham, Birmingham (GB)

( * ) Notice: Subject to any disclaimer, the term of this patent is extended or adjusted under 35 U.S.C. 154(b) by 952 days.

(21) Appl. No.: 16/603,504

(22) PCT Filed: Apr. 9, 2018

(86) PCT No.: PCT/GB2018/050941
§ 371 (c)(1),
(2) Date: Oct. 7, 2019

(87) PCT Pub. No.: WO2018/185503
PCT Pub. Date: Oct. 11, 2018

(65) Prior Publication Data
US 2021/0088507 A1    Mar. 25, 2021

(30) Foreign Application Priority Data

Apr. 7, 2017 (GB) .................................... 1705640
Nov. 9, 2017 (GB) .................................... 1718526

(51) Int. Cl.
*C12Q 1/00* (2006.01)
*G01N 33/543* (2006.01)

(52) U.S. Cl.
CPC ....... *G01N 33/543* (2013.01); *G01N 2400/02* (2013.01); *G01N 2458/10* (2013.01)

(58) Field of Classification Search
CPC .................................................. G01N 33/543
See application file for complete search history.

(56) References Cited

U.S. PATENT DOCUMENTS

| 5,998,588 | A | 12/1999 | Hoffman et al. |
| 2003/0142901 | A1 | 7/2003 | Lahann et al. |
| 2007/0225482 | A1 | 9/2007 | Camarero et al. |

FOREIGN PATENT DOCUMENTS

| WO | 03018854 | A2 | 3/2003 |
| WO | 03055590 | A2 | 7/2003 |
| WO | 2005090981 | A2 | 9/2005 |
| WO | 2007030444 | A2 | 3/2007 |

OTHER PUBLICATIONS

International Search Report for PCT/GB2018/050941 dated Jul. 13, 2018.
Search Report under Section 17(5) for GB application No. GB1705640.9 dated Jan. 16, 2018.
Search Report under Section 17(5) for GB application No. GB1718526.5 dated Aug. 30, 2018.
European Examination Report of European Application No. 8717685.4 dated Jan. 11, 2021.
Lashkor, Minhaj, et at."Switching specific biomolecular interactions on surfaces under complex biological conditions." Analyst 139, No. 21 (2014): 5400-5408.
Mendes, Paula M. "Stimuli-responsive surfaces for bio-applications." Chemical Society Reviews 37, No. 11 (2008): 2512-2529.
Yeung, Chun L., et al. "Modulation of biointeractions by electrically switchable oligopeptide surfaces: structural requirements and mechanism." vol. 1., No. 2 (2014): 1300085.
Yeung, Chun L., et al. "Tuning specific biomolecular interactions using electro-switchable oligopeptide surfaces." Advanced Functional Materials 20, No. 16 (2010): 2657-2663.
Pranzetti, Alice, et al. "Direct observation of reversible biomolecule switching controlled by electrical stimulus." Advanced materials interfaces 1, No. 5 (2014): 1400026.
Pranzetti, Alice, et al. "An electrically reversible switchable surface to control and study early bacterial adhesion dynamics in real-time." Advanced materials 25, No. 15 (2013): 2181-2185.
Cantini, Eleonora, et al. "Electrically responsive surfaces: experimental and theoretical investigations." Accounts of chemical research 49, No. 6 (2016): 1223-1231.
Lashkor, Minhaj, et al. "Electrically-driven modulation of surface-grafted RGD peptides for manipulation of cell adhesion." Chemical Communications 50, No. 98 (2014): 15589-15592.
Ding et al., "Size-dependent control of the binding of biotinylated proteins to streptavidin using a polymer shield", Nature, vol. 6833, pp. 59-61 (2001).
Ng et al., "Using an Electrical Potential to Reversibly Switch Surfaces between Two States for Dynamically Controlling Cell Adhesion", Angew. Chem. Int. Ed, vol. 51, pp. 7706-7710 (2012).
Zareie et al., "Temperature-Responsive Self-Assembled Monolayers of Oligo(ethylene glycol): Control of Biomolecular Recognition", Nano, vol. 2, No. 4, pp. 757-765 (2008).
Search Report for corresponding application GB1718526.5 dated Sep. 3, 2018.

*Primary Examiner* — Albert M Navarro
(74) *Attorney, Agent, or Firm* — Caesar Rivise, PC

(57) ABSTRACT

A stimuli-responsive surface (3) comprising a substrate (20) on which is located a switchable molecule (2) which has a functional moiety (22) associated therewith, wherein the switchable molecule (2) has a first equilibrium state (2A) in which access to the functional moiety (22) is inhibited and a second stimulated state (2B), in which access to the functional moiety (22) is permitted.

16 Claims, 15 Drawing Sheets

STIMULI-RESPONSIVE SURFACES

CROSS-REFERENCE TO RELATED APPLICATIONS

This application is a U.S. National Phase Application of PCT/GB2018/050941, filed Apr. 9, 2018, which claims priority to GB 1705640.9 filed Apr. 7, 2017 and GB 1718526.5 filed Nov. 9, 2017, the contents of which applications are incorporated herein by reference in their entireties for all purposes.

BACKGROUND OF THE INVENTION

This invention relates to stimuli-responsive surfaces and, in particular, although not exclusively, to biosensors incorporating stimuli-responsive surfaces.

It is known that stimuli-responsive surfaces can regulate specific biomolecular interactions between bound biomolecules and analytes. Surfaces with switchable properties have widespread uses, for example, in analytical techniques ranging from environmental monitoring to biotechnological and medical applications. One such example is real-time bioreactor monitoring, which is essential for effective bioprocess control. There is a desire to produce stimuli-responsive surfaces that can monitor a wide range of bioreactions in real-time, without the need for material withdrawal for external analysis, thereby reducing the risk of contamination. Additionally, there is a desire for biosensors that are properly able to function under complex biological conditions, without the need to process the sample prior to analysis.

It is known to use electrically switchable self-assembled monolayers (SAMs) to regulate molecular interactions, for example, between biotin and NeutrAvidin (Mendes, P. et al, *Analyst,* 2014, 139, 5400-5408). This system is based on a surface-bound 4-mer of lysine covalently linked at its terminus to a biotin molecule, in this system an electric potential is required to hold the surface in an inactive state (bent chain). Removal of the electrical stimulus switches the surface, via a conformational change, from the inactive state (bent chain) to an active state (straight chain). Although this system is effective for covalent attachment of relatively small biosensors such as biotin (RMM=244.31 $g \cdot mol^{-1}$), it has proven challenging in use with larger biomolecules, such as proteins, due to the conformational change required for switching between the inactive and active states, We believe that the energy barrier for this type of conformational change is high and thus results in unacceptably low switching efficiencies.

Accordingly, there is a desire for stimuli-responsive surfaces capable of accommodating large biomolecules such as proteins or nanobodies as well as smaller molecules, with high switching efficiencies, for example for use as biosensors.

A first aspect of the invention provides a stimuli-responsive surface comprising a substrate on which is located a switchable molecule which has a functional moiety associated therewith, wherein the switchable molecule has a first equilibrium state in which access to the functional moiety is inhibited and a second stimulated state, in which access to the functional moiety is permitted.

A second aspect of the invention provides a method of accessing a functional moiety, the method comprising locating on a surface a switchable molecule which has a functional moiety associated therewith, the switchable molecule having a first, equilibrium, state in which access to the functional moiety is inhibited, applying a stimulus to cause the switchable molecule to adopt an active state whereby access to the functional moiety is permitted.

Advantageously, the stimulus is applied to the switchable molecule to permit access to the functional moiety. This is beneficial because it allows selective access whilst, in the first, equilibrium (non-stimulated state), access is inhibited.

As used herein, the term "access is permitted" means that a further species is able to interact, e.g. interact chemically, with the functional moiety when the switchable molecule adopts its active state. The term "access is inhibited" will be construed accordingly and may include partial and/or total inhibition. For example, in the equilibrium state a further species may be able to interact to only a minor degree with the functional moiety, or may not be able to interact therewith at all. Even if there is a degree of interaction, e.g. binding, between the functional moiety and further species, before the stimulus is applied, the interaction, e.g. binding, may simply provide a baseline from which, upon application of the stimulus, the response will be measured.

As used herein, the term 'associated with' means that the one or more switchable molecules are in such spatial proximity to the functional moiety so as to inhibit access to the functional moiety in the equilibrium state and permit access to the functional moiety in the stimulated state. The inhibition to the functional moiety may be caused by electrostatic and/or ionic interactions between the switchable molecule and the functional moiety. Additionally or alternatively, the inhibition to the functional moiety may be caused by steric hindrance provided by the switchable molecule. The switchable molecule and the functional moiety need not be bonded, e.g. covalently bonded, together, although they may be.

In the present invention, application and subsequent removal of a stimulus causes a reversible conformational change in between the first equilibrium state in which access to the functional moiety is inhibited and a second stimulated state in which access to the functional moiety is permitted. The conformation change between the first equilibrium state and the second equilibrium state may remove hindrance, for example steric hindrance, which causes access to the functional moiety to be blocked in the first equilibrium state, but access to be permitted in the second equilibrium state.

In an embodiment, the switchable molecule comprises an anchoring moiety to locate the switchable molecule on, for example to anchor the switchable molecule to, the substrate.

In embodiments, the functional moiety is connected to the substrate via a connecting group.

In an embodiment, the switchable molecule has a connecting site to bond the functional moiety to the switchable molecule. The connecting group may comprise or be the connecting site.

The functional moiety may be or may comprise a bioactive moiety, for example a bioactive molecular moiety.

The substrate may be conductive or may comprise or may have located thereon a conductive layer, for example the substrate may be formed from or may comprise a layer formed from a metal or from a conductive ceramic material. For example, the substrate or a layer thereof or located thereon may comprise gold, silver, copper or other conductive metals, or indium tin oxide (ITO), fluorine-doped tin oxide (FT©) or other conductive refractory materials, for example conductive oxide materials such as doped $TiO_2$ or doped $ZrO_2$.

The anchoring moiety or anchoring group may be selected to specifically bind to a particular substrate, for example a particular conductive material or layer.

The stimulus may be an electrical stimulus. For example, where the substrate is conductive or comprises a conductive layer, applying an electrical potential to the substrate or the conductive layer may cause the switchable molecule to adopt its second stimulated state, whereby access to the functional moiety is permitted.

Alternatively, the switchable molecule may be able to transition from the first state to the second state using a different stimulus, for example the switchable molecule may be arranged to transition from one state to another upon exposure to electromagnetic radiation, for example visible, infrared or ultra violet radiation.

In some embodiments the switchable molecule is able to transition from the first to the second state upon exposure to an optical or temperature stimulus.

Preferably, the switchable molecule is able to transition from the first state to the second state and vice versa, i.e. the switching from state-to-state may be reversible by applying and removing the associated stimulus.

The switchable molecule may comprise a shielding portion, the shielding portion being configured upon application of a stimulus to cause the switchable molecule to transition from the first state to the second state.

The switchable molecule may comprise a peptide.

The switchable molecule may comprise a connecting portion.

In an embodiment, the switchable molecule comprises one or more peptide segments, for example, a first, second, third, or fourth, peptide segment. By peptide segment, we mean two or more amino acids covalently bonded together by means of a peptide bond.

In an embodiment, the first peptide segment provides the connecting portion and/or the second peptide segment provides the shielding portion.

The connecting portion may comprise the or an anchoring moiety or group and/or the or a connecting site.

In an embodiment, the connecting portion is the first peptide segment. Where the connecting portion is the first peptide segment, the first peptide segment may have substituents to provide the connecting site and/or the anchoring moiety or group.

The first peptide segment may comprise or be a cyclic peptide, for example a peptide or cyclic peptide comprising functionalised amino acid residues. The cyclic peptide may comprise 5, 6, 7, 8, 9 or 10 or fewer or more functionalised amino acid residues. The functionalised amino acid residues in the cyclic peptide may be lysine, or alternatively may be one or a combination of other functionalised amino acids.

The second peptide segment may comprise lysines, aspartic acids, arginine, histidine or glutamic acid, for example oligolysines, oligoaspartic acids, oligoglutamic acid, an oligoarginine or an oligohistidine.

In an embodiment, the second peptide segment may be an arm or side chain of or from the first peptide segment.

In embodiments, there may be further provided a third peptide segment which may be an arm or side chain of or from the cyclic peptide segment. The third peptide segment may provide a further shielding portion.

The second and third peptide segments, where present may be formed from the same or different peptides, for example in the number of peptide residues and/or the identity of the peptides. For example, the second peptide segment may be composed of five or more lysine resides. Alternatively, the second peptide segment may be composed of five or more aspartic acid resides. In an embodiment the third peptide segment may be composed of five or more lysine resides. Alternatively, the third peptide segment may be composed of five or more aspartic acid resides embodiments. In an embodiment, the second peptide segment is comprised of five or more lysine residues and the third peptide segment is composed of five or more aspartic acid residues.

In alternative embodiments, there may be one or more peptide segments, e.g. two, three, four, five, six, seven, eight, nine, ten or more peptide segments. The one or more peptide segments may be the same structure or comprise different structures to one another. The one or more peptide segments may comprise lysines, aspartic acids, arginine, histidine or glutamic acid, for example oligolysines, oligoaspartic acids, oligoglutamic acid, an oligoarginine or an oligohistidine.

The peptide segments, e.g. the one or more peptide segments, may comprise non-standard amino acids (NSAAs) or unnatural amino acids (UAAs), for example, 2,3-diaminopropionic acid (DAP), or 2,4-diaminobutyric acid (DAB).

The one or more peptide segments may be formed from the same or different peptides, for example in the number of peptide residues and/or the identity of the peptides. For example, the peptide segments may be composed of five or more lysine resides. Alternatively, the peptide segments may be composed of five or more aspartic acid resides.

In embodiments, the one or more peptide segments may provide the shielding portion.

The shielding portion may possess multiple charged moieties along its length, or indeed moieties which become charged at certain conditions, which are attracted to or repelled from the conductive surface upon application of an electrical potential. For example, lysine may become protonated at physiological pH conditions, thereby providing the conditions at which lysine is attractable to a negative potential.

The anchoring moiety or group may comprise a thiol group to enable the switchable molecule to be anchored to a gold conductive layer or gold substrate. Alternatively, the point of attachment for connection of the switchable molecule to the substrate, for example, an ITO surface, may be achieved by means of a siloxane (Si—O) bond, wherein the anchoring moiety or group comprises a silane group. The anchoring group may comprise an alkyne, which reacts via a copper(I)-catalysed azide-alkyne cycloaddition (CuAAC or 'click' chemistry) with an azide on the substrate. Alternatively, the substrate may be functionalised with the alkyne groups, and the anchoring moiety or group may comprise an azide group, the two functional groups reacting together to anchor the switchable molecule to the substrate.

In embodiments comprising a connecting site, the connecting site may be functionalised to provide a site to bind to the required functional moiety.

Furthermore, the anchoring moiety or group of the switchable molecule may comprise a thiol group, which may react with the maleimide group of the functionalised substrate to form a thiol-maleimide bond.

The functional moiety may be a single-domain antibody (e.g. a nanobody). Nanobodies exhibit a length down to 2-3 nm, and molecular weights of between 12-15 kDa, which are much smaller than those of antibodies (150-160 kDa). For example, if the functional moiety is a nanobody, the nanobody may be Vascular Cell Adhesion Molecule-1 (NbVCAM1), which is an atherosclerotic biomarker. Alternatively, the functional moiety may be a protein, a hormone, or a vitamin or another type of biomolecule. The functional moiety may be a small molecule, for example a coenzyme, one example is biotin. Preferably, the functional moiety does not undergo a conformation change when the switchable molecule transitions between the first and second state.

Alternatively, the switchable molecule may comprise a non-peptide structure. For example, the switchable molecule and/or the shielding portion may be composed of another type of charged molecular structure, for example, the shielding portion may be composed of a polyelectrolyte, such as poly(sodium styrene sulfonate) (PSS) or polyacrylic acid (PAA), or any other polymer chain possessing a carboxylic acid, amino, sulfonate, phosphate or any other polar or charged group.

In embodiments comprising a connecting site, the point of attachment for connecting the connecting site to the functional moiety may be achieved by a copper(I)-catalysed azide-alkyne cycloaddition (CuAAC or 'click' chemistry). For example, the connecting site may possess the reactant azide moiety and the functional moiety may possess the reactant alkyne moiety. Alternatively, the point of attachment for connecting the connecting site to the functional moiety may be achieved via coupling of a maleimide and a thiol or amine group.

Additionally or alternatively, the functional moiety may comprise a connecting moiety to locate the functional moiety on, for example to anchor or connect, the functional moiety to the substrate. The connecting group may comprise or be the connecting moiety. The connecting moiety may comprise a thiol group to enable the switchable molecule to be anchored to a gold conductive layer or gold substrate. Alternatively, the point of attachment for connection of the functional moiety to the substrate, for example, an ITO substrate, may be achieved by means of a siloxane (Si—O) bond. Alternatively, connection of the functional moiety to the substrate may be achieved by a copper(I)-catalysed azide-alkyne cycloaddition (CuAAC or 'click' chemistry). For example, the substrate may possess the reactant azide moiety and the functional moiety may possess the reactant alkyne moiety.

Alternatively, the connecting moiety to locate and/or anchor the functional moiety on the substrate may be achieved via coupling of a maleimide and a thiol or amine group. In other embodiments, wherein the functional moiety is a protein, or a peptide, the functional moiety may be immobilised to the substrate by reaction of amino groups or acid groups within the protein structure.

In embodiments, wherein the substrate is ITO, glass, or silicon, the substrate may be functionalised with a maleimide silane, for example, silane PEG maleimide. The silane group of the maleimide silane may react with the ITO or glass substrate to form siloxane (Si—O) bonds. The functionalised moiety may comprise a thiol group as the connecting moiety, which may react with the maleimide group of the maleimide-silane functionalised substrate to form a thiol-maleimide bond. In this way, the maleimide silane may form an intermediate connecting moiety between the substrate and the functional moiety. Preferably, the anchoring moiety or group (for locating the switchable molecule on the substrate), and the connecting moiety (for locating the functional moiety on the substrate) are the same type of group, for example, a thiol group.

In embodiments, the surface may be patterned to provide an optimal location for each functional moiety and each switchable molecule on the substrate.

The functional moiety and the one or more switchable molecules may be independently located on the substrate. For example, the functional moiety may comprise a connecting moiety that is separate and independent from the anchoring moiety of the one or more switchable molecules. In embodiments, each functional moiety is associated with plural switchable molecules.

In embodiments, the stimuli-responsive surface may further comprise lateral spacer molecules, for example, short oligo(ethylene glycol) molecules. The oligo(ethylene glycol) molecules may comprise a thiol group for attachment onto the substrate, e.g. a gold substrate.

The stimuli-responsive surface may be deployed as a sensor and the invention relates to a sensor incorporating the stimuli-responsive surface.

The functional moiety may be selected to selectively bind to an analyte of interest. An analyte may be a small organic molecule, an antigen, a protein, or a cell epitope.

Presence or absence of binding of an analyte with the functional moiety may be detected by electrochemical means, for example electrochemical impedance spectroscopy.

A further aspect of the invention provides a method for detecting an analyte, the method comprising applying an electrical potential across a conductive surface to initiate a conformational change in a switchable molecule from a first equilibrium state to a second active state thereby to expose a functional moiety, preferably a bioactive molecular moiety, associated with the switchable molecule and exposing the bioactive molecular moiety to a substance to be analysed.

A further aspect of the invention provides a method of fabricating a stimuli-responsive surface, the method comprising step a) locating a functional moiety on a substrate with a connecting moiety, and step b) locating plural stimuli responsive switchable molecules on the substrate with an anchoring group. The steps may be performed simultaneously, or at different times, for example, step a) may be performed before step b). Alternatively, step b) may be performed before step a).

The method of fabricating a stimuli-responsive surface may further comprise using a different ratio of functional moiety to stimuli responsive switchable molecules. The use of different ratios may lead to different types of self-organisation and/or distribution of the functional moiety and the stimuli-responsive switchable molecule across the substrate. For example, a greater molar quantity of switchable molecules may be used in comparison to functional moieties.

The method of fabricating a stimuli-responsive surface may further comprise step c) locating an oligo(ethylene glycol) spacer on the substrate. Step c) may be performed simultaneously with step a) and/or step b), or before, or after, either or both of step a) and step b).

The method of fabricating a stimuli-responsive surface may further comprise applying an electrical potential across the substrate. The use of an electrical potential may be used to vary the density and/or organisation of the functional moieties and the stimuli-responsive switchable molecules.

A yet further aspect of the invention provides a biosensor, the biosensor comprising a surface on which a switchable molecule is located, the switchable molecule having associated therewith a functional moiety, preferably a bioactive molecular moiety, and having a first equilibrium state in which access to the functional moiety is inhibited and a second stimulated state, in which access to the functional moiety is permitted, the switchable molecule being able to transition from the first state to the second state upon application of a stimulus.

The biosensor may comprise means to apply an electric potential to the surface whereby the switchable molecule is able to transition from the first state to the second state.

The stimuli-responsive surface may be employed as a biosensor in a bioreactor for long-term continuous and/or intermittent sampling.

A still further aspect of the invention provides a switchable molecule, the molecule comprising a first peptide segment, a second peptide segment and optionally a third peptide segment, the first peptide segment comprising an anchoring moiety or group for securing the molecule to a surface and/or a connecting site for association therewith of a functional moiety capable of binding an analyte, the second peptide segment and/or third peptide segment (where present) being able, upon application of a stimulus, to transition from an equilibrium state in which access to an associated functional moiety is inhibited to an active state in which access to an associated functional moiety is permitted.

A still further aspect of the invention provides a switchable molecule, the molecule comprising a peptide segment, the peptide segment comprising an anchoring moiety or group for securing the switchable molecule to a surface, the switchable molecule being operable to adopt a first equilibrium state and a second stimulated state. The peptide segment being able, upon application of a stimulus, to transition from the equilibrium state the second stimulated state.

The switchable molecule may have a functional moiety associated therewith, the functional moiety preferably comprising a connecting moiety or group for securing the functional moiety to the surface, wherein the functional moiety is capable of binding an analyte.

In order to better understand the invention, and by way of non-limiting example only, reference is made to the following drawings, in which.

Figure 1:
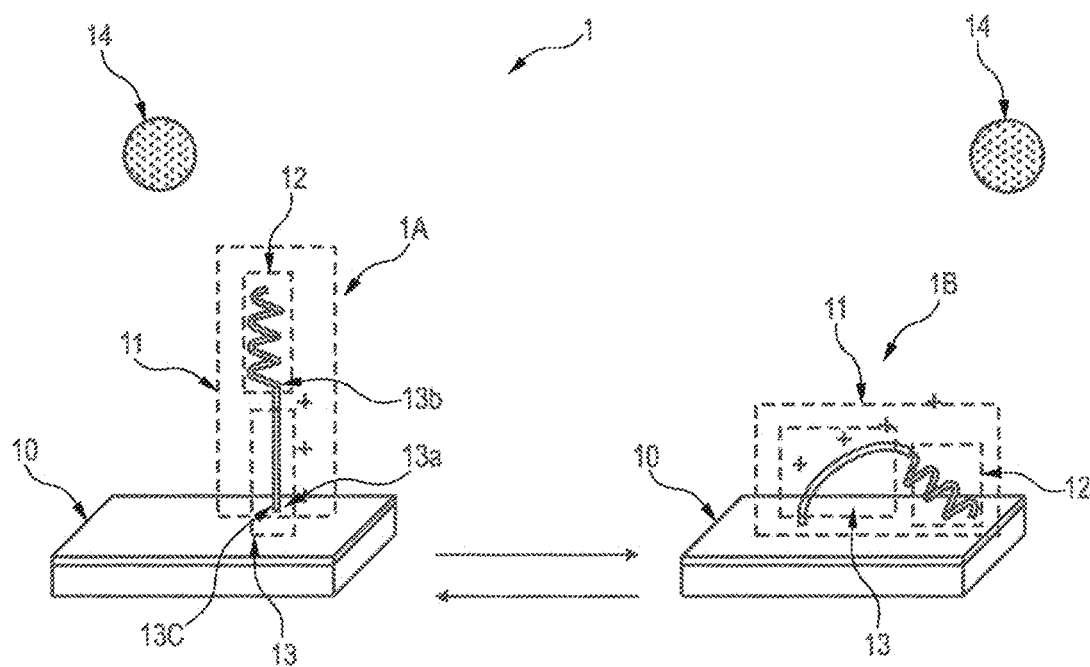
FIG. 1 is a schematic representation a stimuli-responsive surface of the prior art.

Turning first to FIG. 1 there is shown an electrically responsive surface 1 of the prior art, which regulates the molecular interaction between biotin and NeutrAvidin. The electrically responsive surface 1 is shown in an equilibrium state 1A and an inhibited state 1B. The electrically responsive surface 1 comprises a conductive substrate 10, a switchable molecule 11, a functional moiety 12, a peptide 13, and an anchoring group 13C. The switchable molecule 11 comprises the functional moiety 12, which in this case is biotin, and the peptide 13, which in this case is an oligolysine. The anchoring group 13C is bound to the conductive substrate 10 at its proximal end 13a, and is covalently bound to the peptide 13 and thence to the functional moiety 12 at its distal end 13b. The electrically responsive surface 1 is immersed in a solution containing the analyte 14, which in this case is NeutrAvidin.

The peptide 13 is an oligolysine comprising, for example, four lysine residues, each of which possesses a single positive charge, at pH 7, by virtue of the protonated α-amino group, so that the peptide 13 has positively charged moieties along its length.

The anchoring group 13C comprises a thiol group, and the conductive substrate 10 comprises a gold surface. The peptide 13 is attached by the anchoring group 13C to the conductive substrate 10 by a sulphur-gold bond.

In use, the electrically responsive surface 1 is maintained in its inactive state 1B by maintaining a negative potential across the conductive surface 10. In this state the analyte 14 is unable to interact with the functional moiety 12. In order to configure the electrically responsive surface 10 so that the functional moiety 12 is able to interact with the analyte 14 it is necessary to either remove the potential or to apply a positive potential, thereby to allow the switchable molecule 11 to adopt the active state 1A. Accordingly, in the inhibited state 1B, no analyte binding is permitted.

As described above, there are a number of disadvantages associated with this prior art system. For example, it is difficult to utilise this system with large biomolecules, such as nanobodies or proteins, because the large conformational change required of the biomolecule leads to low switching efficiencies. Additionally, the inhibited state 1B requires a negative potential to be applied, to ensure the continued interaction of the surface with the switchable molecule 11 to restrict activity of functional moiety 12.

Figure 2:
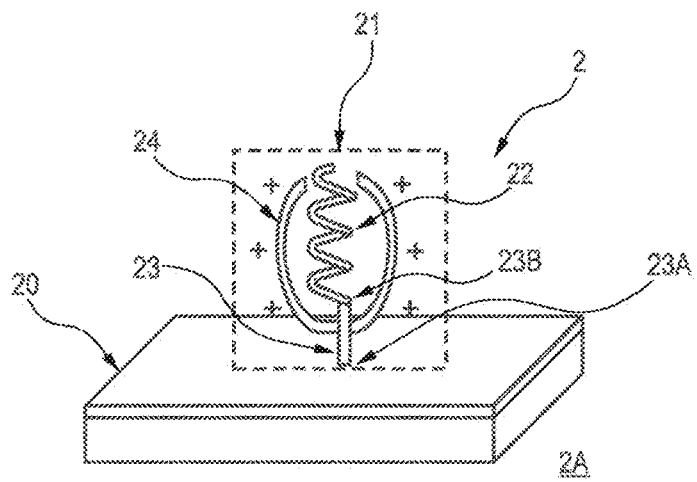
FIG. 2 is a schematic representation of a substrate-bound switchable molecule according to a first embodiment of the invention.

Referring now to FIG. 2, there is shown a substrate-bound switchable molecule 2 of the present invention, comprising a substrate 20, a switchable molecule 21, a functional moiety 22, a connecting portion 23, and a shielding portion 24. The connecting portion 23 comprises an anchoring group 23A and a connecting site 23B. The connecting portion 23 is connected to the shielding portion 24. The connecting portion 23 is also independently connected to the substrate 20 via the anchoring group 23A, and the functional moiety 22 via a connecting site 23B. The substrate-bound switchable molecule 2 is shown in its equilibrium state 2A in which the stimulus is off.

Figure 3:
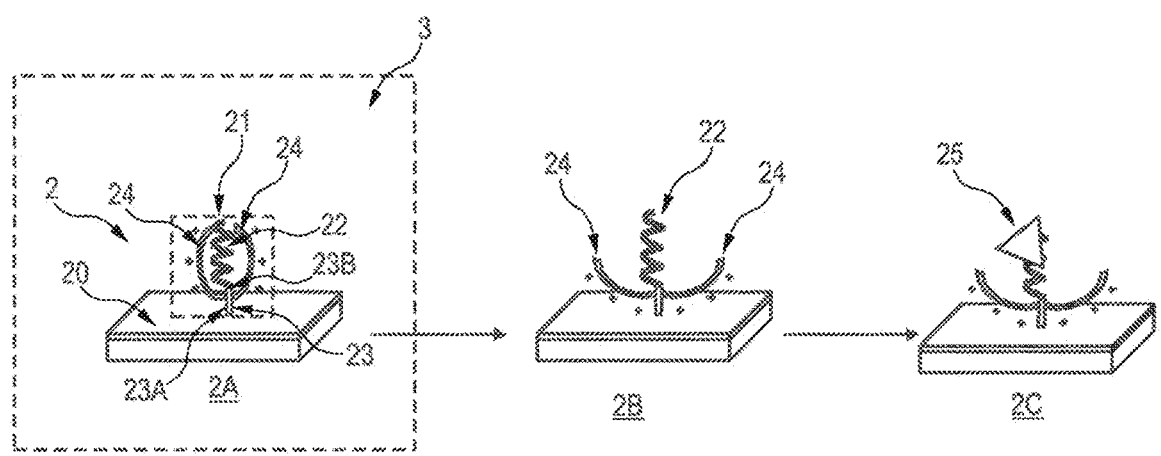
FIG. 3 is a schematic representation of the system of the invention.
Figure 4A:
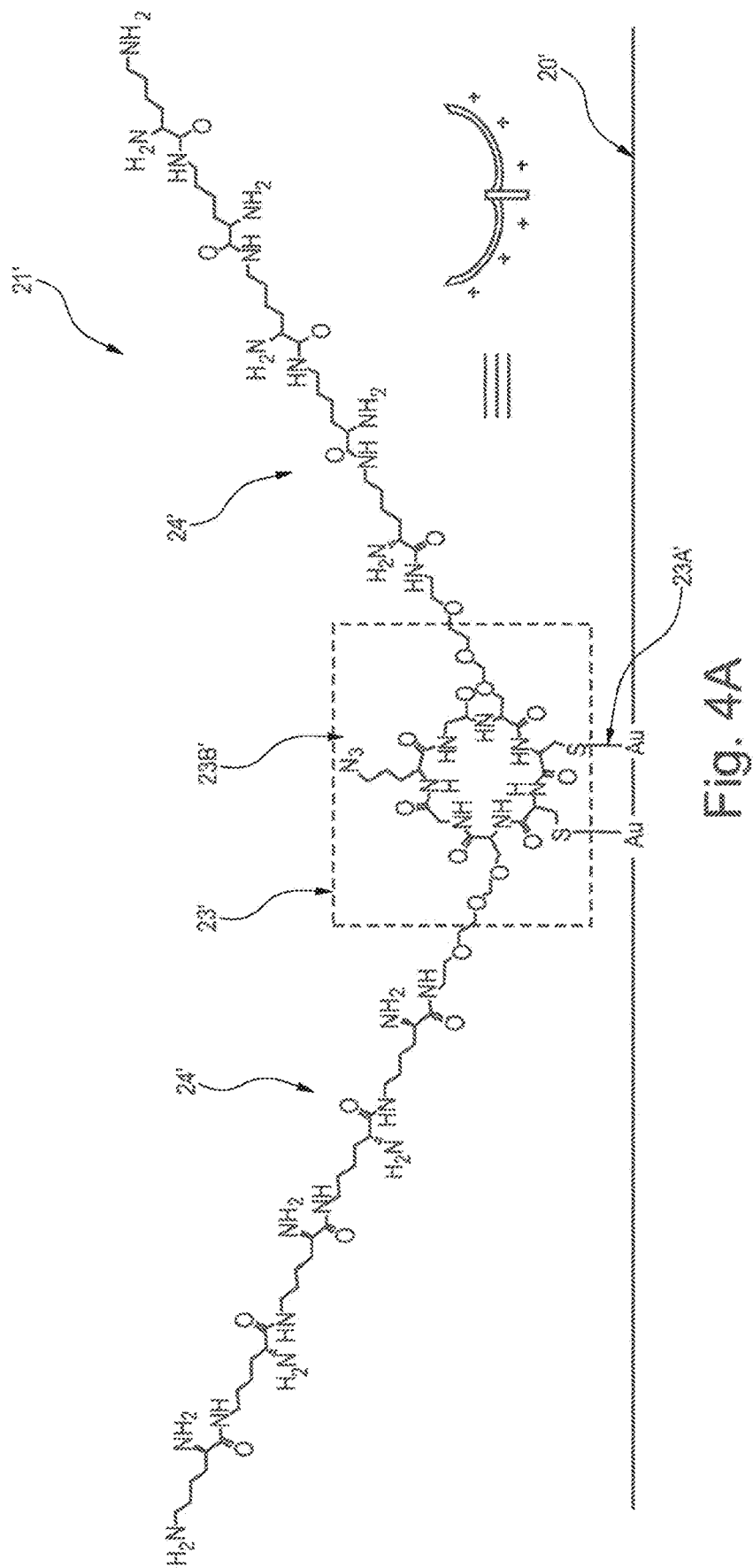
FIG. 4A is a chemical structure of a first embodiment of a switchable molecule.
Figure 4B:
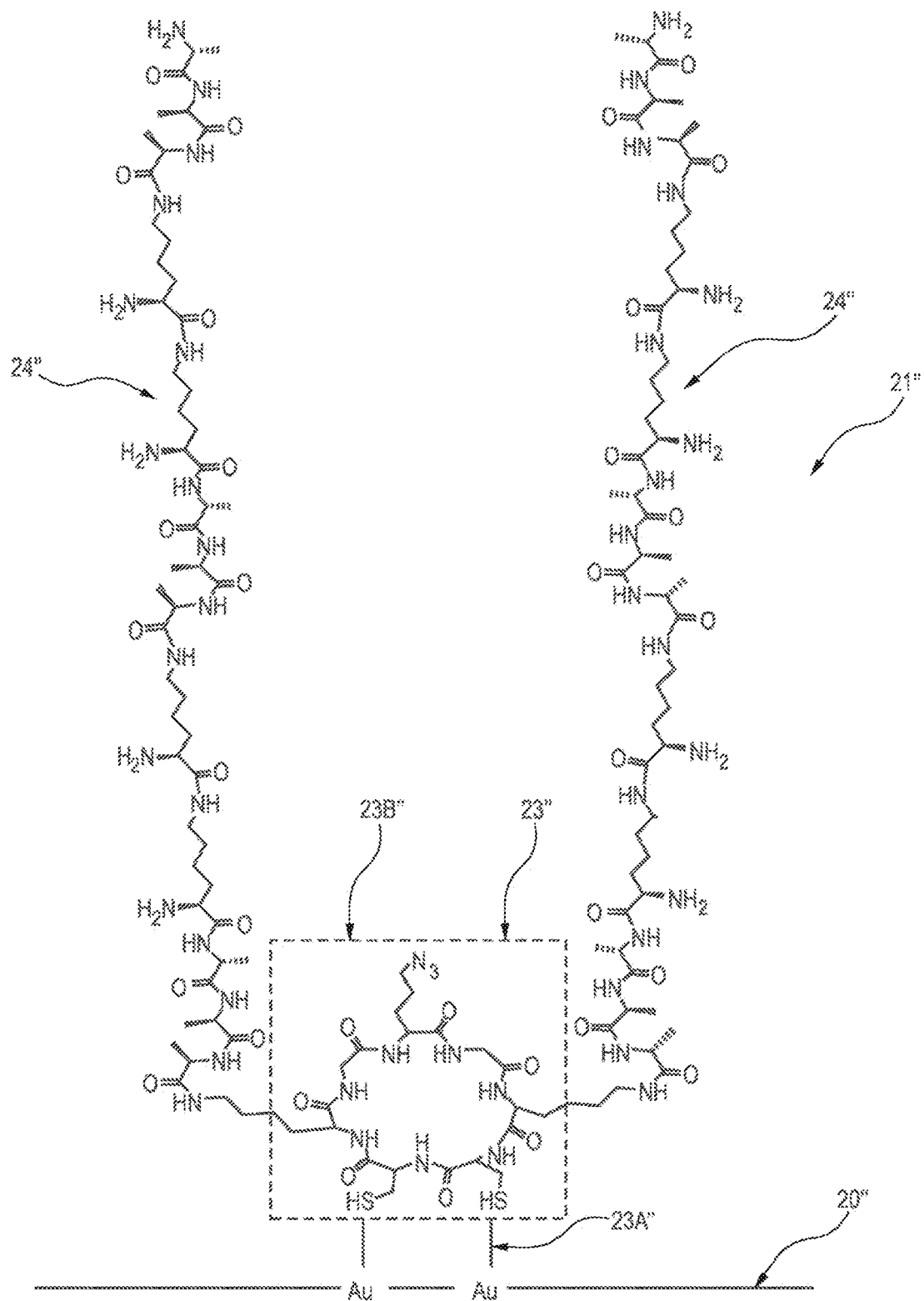
FIG. 4B is a chemical structure of a second embodiment of a switchable molecule.
Figure 4C:
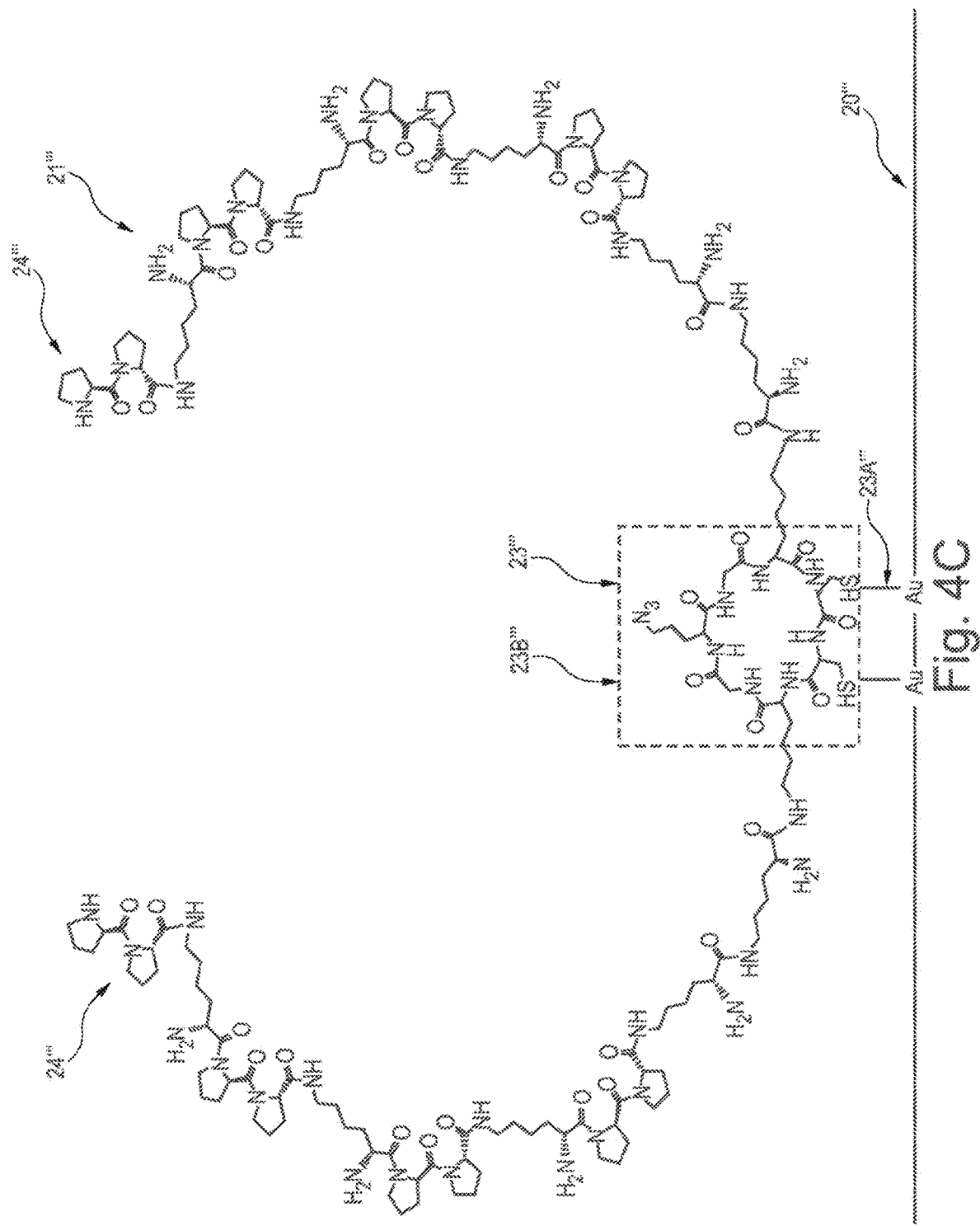
FIG. 4C is a chemical structure of a third embodiment of a switchable molecule.
Figure 4D:
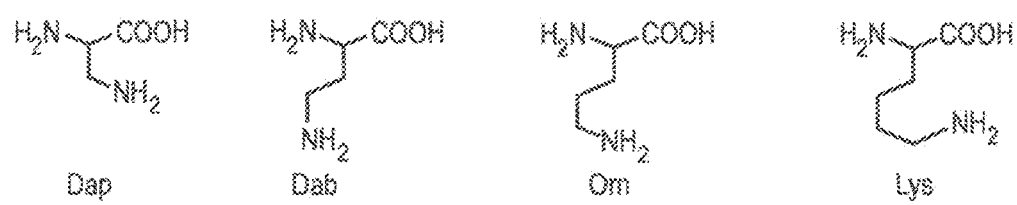
FIG. 4D is chemical structures of alternative amino acids for use in fabricating the switchable molecule.

In FIG. 3 there is shown a stimuli-responsive surface 3 of the present invention comprising the substrate-bound switchable molecule 2 and comprising the substrate 20, the switchable molecule 21, the functional moiety 22, the connecting portion 23, the anchoring group 23A, the connecting site 23B and the shielding portion 24. Additionally, there is shown a target analyte 25. The switchable molecule 21 is shown in the equilibrium state 2A, the stimulated state 2B, and the analyte-bound state 2C.

In use, with no stimulus is applied, the electrically switchable molecule 21 is in the equilibrium state 2A, in which access to the functional moiety 22 is inhibited. This is by means of the shielding portion 24, which conceals the functional moiety 22, or at least the or each active or binding site thereof. Upon application of a stimulus, the switchable molecule 21 is caused to transition from the equilibrium state 2A to the stimulated state 2B. As can be seen, in the stimulated site 2B access to the functional moiety 22 (or at least to the (or at least one of the) active or binding site thereof is permitted. The shielding portion 24 ceases to conceal or inhibit access to the functional moiety 22, and the electrically switchable molecule 21 is now in an active state.

In some embodiments, the stimuli-responsive surface 2 may be immersed in a medium containing the target analyte 25. In the stimulated state 2B, the target analyte 25 has access to, and may therefore bind to the functional moiety 22, the response of which may be measured to record the presence of the target analyte 25 in solution, or to quantify the concentration of target analyte 25 in the solution.

In an embodiment, the stimuli-responsive surface 3 is an electrically-responsive surface. The substrate 20 comprises a conductive layer of gold, the functional moiety 22 is a nanobody, the connecting portion 23 is a cyclic peptide, and the shielding portion 24 comprises two individual oligolysine chains.

At physiological pH conditions, the oligolysine chains of the shielding portion 24 have multiple positive charges along their length by virtue of the protonated α-amino groups on each lysine residue. The length of the oligolysine peptides (i.e. the number of lysine residues) is selected to be appropriate to the functional moiety 22, that is to be sufficient to provide an adequate shield to inhibit access of the analyte to the active site of the functional moiety 22.

In use, under open-circuit conditions i.e. no potential applied, the oligolysine chains (shielding portion 24) inhibit access to the nanobody (functional moiety 22). Without wishing to be bound by theory, it is believed that the positively charged lysine residues of the oligolysine peptides form electrostatic interactions with the peptide chains of the nanobody 22, thereby allowing the oligolysine peptides of each shielding portion 24 to fold around the nanobody (functional moiety 22) to inhibit access. This limits the ability of the target analyte to bind to the nanobody (functional moiety 22) due to steric hindrance. It should be noted that access to the nanobody (functional moiety 22) is inhibited even when it the oligolysines are only partially folded around the nanobody (functional moiety 22).

Upon application of a negative potential to the conductive layer of gold of the surface 20, the positively charged oligolysine chains are attracted towards the negatively charged conductive layer of gold of the surface 20. This causes the oligolysine chains (shielding portion 24) to undergo a conformational change to unfold from around the nanobody (functional moiety 22). Without wishing to be bound by theory, it is believed that the negative potential provides enough energy to overcome any electrostatic interactions between the oligolysine peptides and the nanobody. The switchable molecule 21 is thus provided in the stimulated state 2B, in which access to the functional moiety 22 is permitted. This process may be reversible; reversing the stimulus applied to the electrically responsive surface (i.e. removing the electrical potential) may transition the switchable molecule 21 from the stimulated state 2B back to the equilibrium state 2A.

In the stimulated state 2B, access to the nanobody (functional moiety 22) is permitted and is therefore able to bind to the target analyte 25 to adopt the analyte-bound state 2C.

Referring now to FIG. 4A there is shown a chemical structure of a switchable molecule 21' of the present invention bound to a substrate of a conductive layer of gold 20'.

The switchable molecule 21' comprises as the connecting portion 23' a cyclic peptide and, as a shielding portion 24', a pair of oligolysine chains. The connecting portion 23' comprises, as an anchoring group 23A to connect the cyclic peptide to the conductive layer of gold 20' a thiol or sulphur moiety. The connecting portion 23'A also comprises, as a connecting site 23B', an azide moiety for location of the functional moiety (not shown). As shown, the switchable molecule 21' is configured in the active state.

In order to fabricate the switchable molecule 21', a cyclic peptide with side chains is created using peptide synthesis protocols, which comprise the oligolysines double-arm molecules, an azide moiety and two thiol groups. The presence of the thiol groups allows for the formation of two strong gold-thiol linkages per cyclic peptide derivative. The presence of the azide moiety allows for conjugation with an alkyne moiety in an engineered nanobody via copper(I)-catalyzed azide-alkyne cycloaddition (CuAAC) "click" chemistry.

There is a broad range of nanobodies commercially-available for detecting different analytes with high specificity and affinity. However, their immobilization in a biosensor would typically rely in a random conjugation either using the carboxylic acid or amino groups available in the nanobody itself. This would lead to the immobilization of some nanobodies in a configuration where the binding sites would never be available for analyte binding. Thus, and in order to maximise the use of the nanobodies in the biosensor, we carry out a covalent and uniformly oriented coupling of the nanobody, thereby to maximise the available binding sites.

Referring now to FIG. 4B, there is shown a further embodiment of a chemical structure of a switchable molecule 21" of the present invention bound to a substrate of a conductive layer of gold 20". The switchable molecule 21" is similar to that shown in FIG. 4A, and like references are designated with a prime (') and will not be described further. In this embodiment, the shielding portion 24" comprises alanine (ala) and lysine (lys) residues, in the following sequence (beginning from the connecting portion 23") ala-ala-ala-lys-lys-ala-ala-ala-lys-lys-ala-ala-ala.

Referring now to FIG. 4C, there is shown a further embodiment of a chemical structure of a switchable molecule 21''' of the present invention bound to a substrate of a conductive layer of gold 20'''. The switchable molecule 21''' is similar to that shown in FIGS. 4A and 4B, and like references are designated with a prime (') and will not be described further. In this embodiment, the shielding portion 24''' comprises lysine (lys) and proline (pro) resides, in the following sequence (beginning from the connecting portion 23''') lys-lys-pro-pro-lys-pro-pro-lys-pro-pro-lys-pro-pro.

Referring now to FIG. 4D, there is shown four amino acid resides (Dap), (Dab), (Orn), and (Lys), wherein (Dap) is 2,3-diaminopropionic acid, (Dab) is 2,4-diaminobutyric acid, (Orn) is ornithine, and (Lys) is lysine. In embodiments, the shielding portion 24 may comprise an oligopeptide of one or a combination of the amino acids (Dap), (Dab), (Orn), and (Lys). Advantageously, the rigidity of the shielding portion 24 may be tuned by fabrication using one or a combination of these amino acids. In general, the rigidity of oligopeptides comprising one type of amino acid is as follows (Dap)>(Dab)>(Orn)>(Lys), i.e. an oligopeptide comprising only (Dap) monomers will have greater rigidity compared to an oligopeptide comprising only (Lys) monomers. In addition, the rigidity of different parts or regions of the shielding portion 24 may be altered or 'tuned' depending on the composition of amino acids in the oligopeptide chain, wherein one type of amino acid, or a specific combination or sequence of amino acids, are used to provide different rigidity in different regions of the shielding portion 24.

Figure 5:
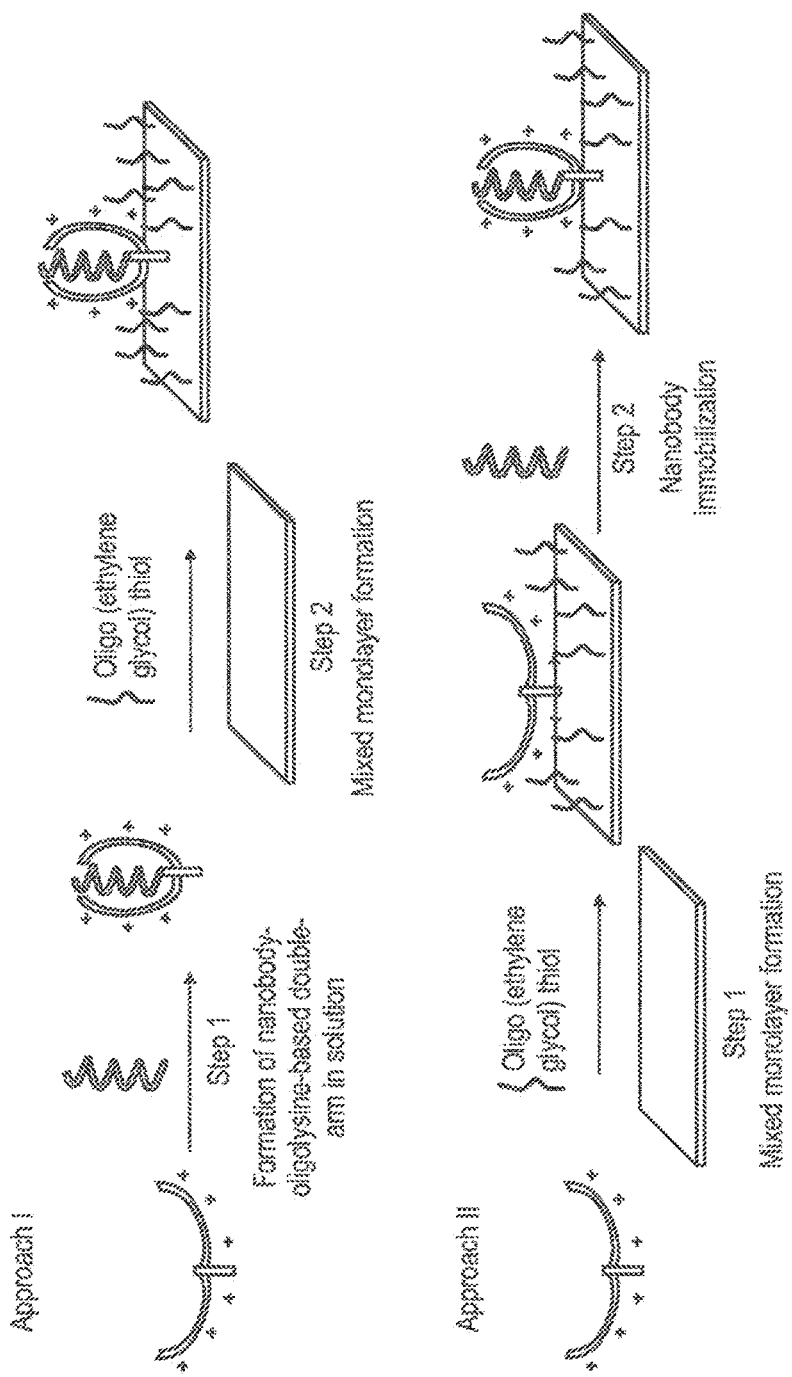
FIG. 5 is a schematic representation of a method of forming the switchable molecule of the invention.

Referring now to FIG. 5, there is shown two methods (Approach I, Approach II) for the formation of the stimuli-responsive surface 3 of the invention.

In the first approach (Approach I), the 'click reaction' in solution is used to link the oligolysine-based double-arm system to the nanobody and then form the nanobody-oligolysine-based double-arm monolayers on gold substrates.

The second approach (Approach II) requires binding of the oligolysine-based double-arm system to the substrate and the subsequent binding of the nanobody to the switchable molecule.

In both approaches, mixed monolayers will be formed using a short oligo(ethylene glycol) thiol with either the nanobody-oligolysine-based double-arm system or oligolysine-based double-arm system, as appropriate. The short oligo(ethylene glycol) molecule is employed as a lateral spacer to allow sufficient spatial freedom for synergistic molecular reorientation of the surface-bound oligolysine-based double-arms.

In this fashion a surface is created with a high number of switchable molecules per surface area but not dense enough such that conformational change of the molecular double arms is hindered. Apart from having a positive effect on the switching efficiency, the short oligo(ethylene glycol) groups prevent non-specific interactions with the surface.

The modified surfaces are characterized by contact angle to determine wettability, X-ray photoelectron spectroscopy (XPS) to determine the surface elemental composition, ellipsometry to evaluate film thickness and atomic force microscopy (AFM) to characterise the surface morphology. The packing density of the switchable nanobodies on the gold surface is determined by XPS through analysis of elemental ratios as previously described by the inventor (e.g. Chem. Commun. (2014); 50(98); 15589-92). It is also possible to deploy electrochemical surface plasmon resonance SPR (eSPR) to allow the monitoring of surface binding whilst an electrical potential is applied to the surface using a three-electrode electrochemical cell and a potential. The gold surfaces serve as the working electrode, a Pt wire as the counter electrode, and a standard calomel electrode as the reference electrode. While applying a −0.4 V, the gold surfaces with the switchable nanobodies are exposed to recombinant hVCAMI antigen (R & D Systems) and the binding capacity measured as an SPR response. SPR controls are also performed where no potential will be applied (OC conditions). These experiments allow a determination of not only the binding capacity of the switchable nanobodies but also the switching efficiency, which is calculated as the percent difference between the binding capacity (BC) at −0.4 V and OC conditions ($BC_{OC}$) divided by BC at −0.4 V.

Figure 6:
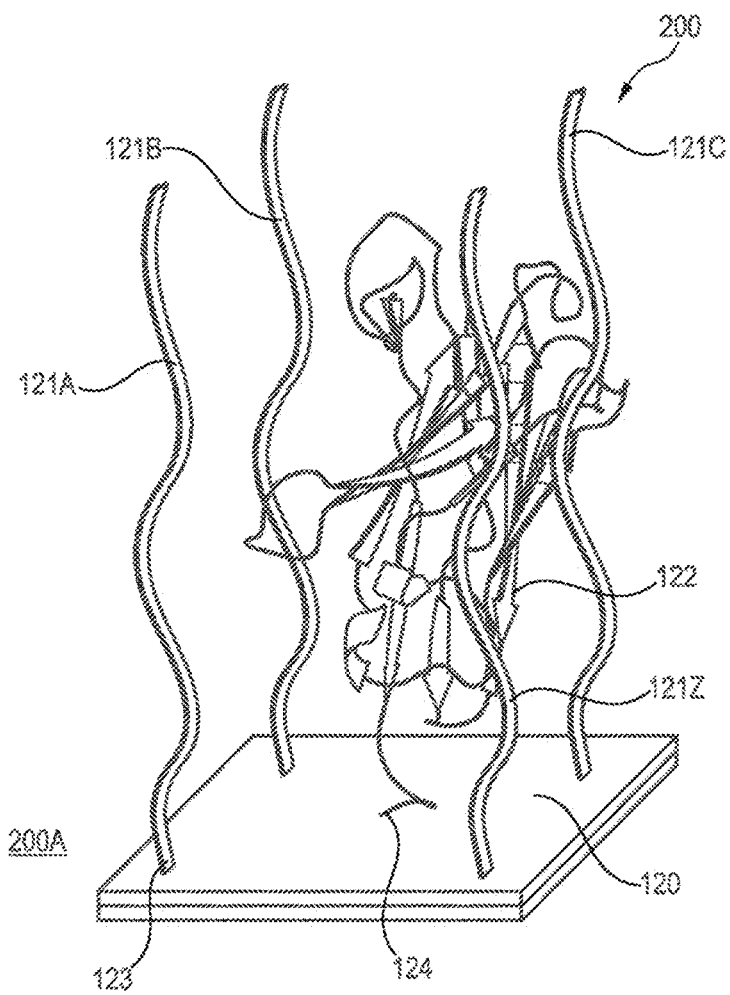
FIG. 6 is a schematic representation of a substrate-bound switchable system according to a further embodiment of the invention.

Referring now to FIG. 6, there is shown a substrate-bound switchable system 200 of the present invention, comprising a substrate 120, a number of switchable molecules 121A, 121B, 121C ... 121Z (only four shown but the number may be larger or smaller), and a functional moiety 122. The switchable molecules 121A, 121B, 121C ... 121Z each comprise an anchoring group 123 (shown only for switchable molecule 121A) by which the switchable molecule 121A is secured to the substrate 120. The functional moiety 122 comprises a connecting moiety 124 by which it is secured to the substrate 120.

The substrate-bound switchable system 200 is shown in its equilibrium state 200A. The equilibrium state is a state of the system in which an activating stimulus is not applied (as will be explained below).

Each switchable molecule 121A, 121B, 121C ..., 121Z is independently connected to the substrate 120 via its respective anchoring group 123 (shown only for switchable molecule 121A). The functional moiety 122 is connected to the substrate 120 via the connecting moiety 124. In this embodiment, the functional moiety 122 is connected to the substrate 120 independently of the switchable molecules 121A, 121B, 121C ... 121Z.

The functional moiety 122 may comprise one or more active or binding sites (not shown).

In the equilibrium state 200A in which the stimulus is not applied, the switchable molecules 121A, 121B, 121C ... 121Z act to shield the functional moiety 122. Specifically, the switchable molecules 121A, 121B, 121C ... 121Z act to shield the active and/or binding site(s) of the functional moiety 122.

Figure 7A:
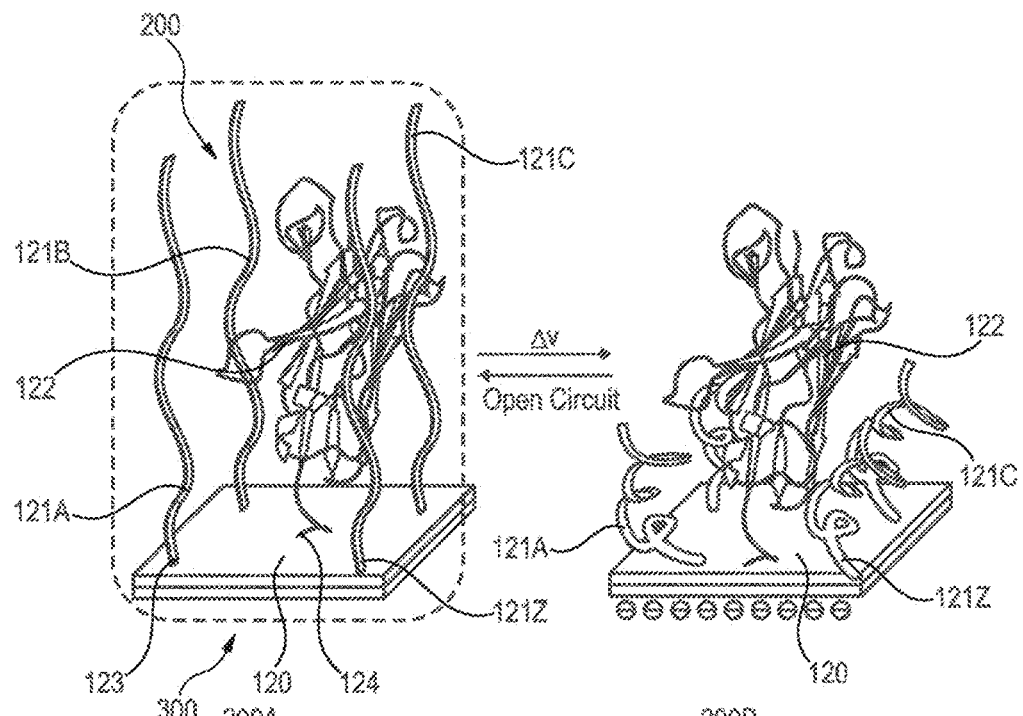
FIG. 7A is a schematic representation of the system of the invention according to a further embodiment of the invention.

In FIG. 7A there is shown the substrate-bound switchable system 200 transitioning between its equilibrium state 200A in which the stimulus is not applied, and in the stimulated state 200B, in which the stimulus is applied.

In use, with no stimulus applied, the switchable molecules 121A, 121B, 121C ... 121Z of the substrate-bound switchable system 200 are in the equilibrium state 200A, in which access to the functional moiety 122 is inhibited. The switchable molecules 121A, 121B, 121C ..., 121Z each have a shielding portion to conceal at least a part of the functional moiety 122, or at least a part of the or each active or binding site thereof. Upon application of a stimulus, the switchable molecules 121A, 121B, 121C ... 121Z are caused to transition from the equilibrium state 200A to the stimulated state 200B.

Figure 7B:
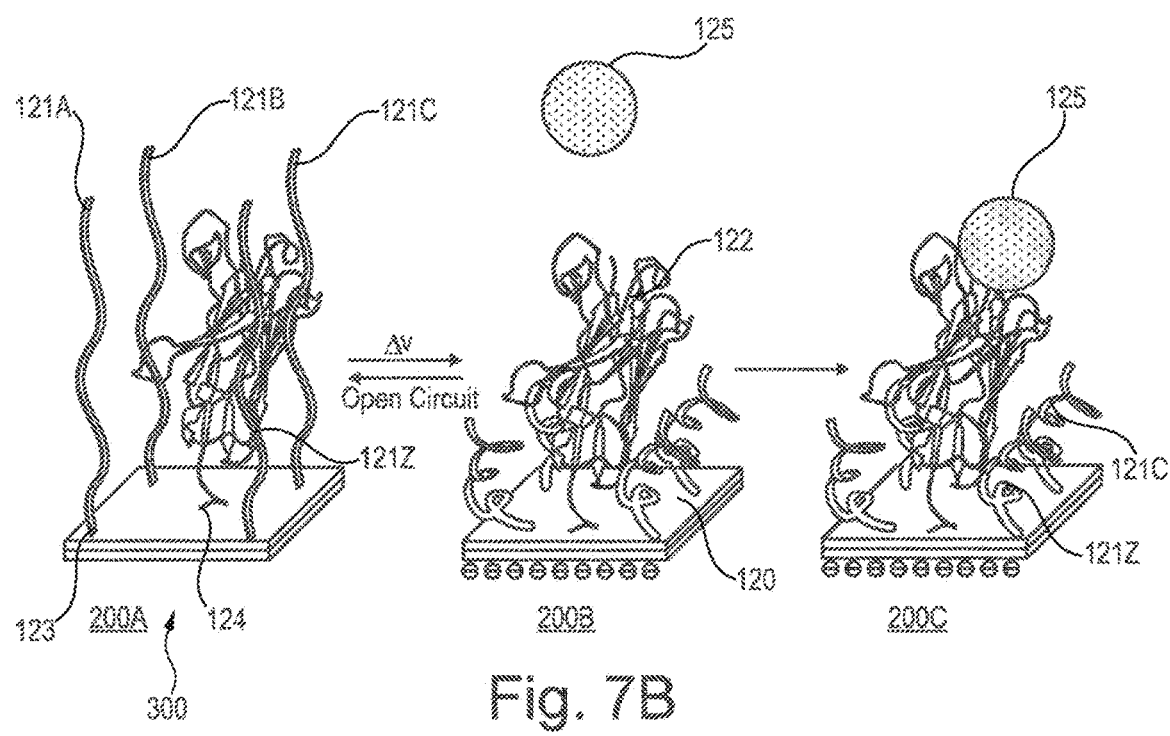
FIG. 7B is a further schematic representation of the system of the invention.

In FIG. 7B there is shown the substrate-bound switchable system 200, which further comprises a target analyte 125. As will be appreciated, with the substrate-bound switchable system 200 in its active or stimulated state, the target analyte 125 is free to bind to the functional moiety 122, as is indicated in the analyte-bound state 200C.

In an embodiment, the substrate 120 is an electrically-responsive surface, wherein the stimulus is an electrical potential Δv, the substrate 120 comprises a conductive layer (e.g. gold), the anchoring group 123 comprises a thiol group, and the connecting moiety 124 also comprises a thiol group, the thiol groups forming sulphur-gold bonds with the substrate 120, each switchable molecule 121A, 121B, 121C ..., 121Z, comprises a peptide chain, for example, a lysine 5-mer peptide chain, and the functional moiety 122 comprises a nanobody.

At physiological pH conditions, the lysine residues in the peptide chain of the switchable molecules 121A, 121B, 121C ... 121Z have multiple positive charges along their length by virtue of the protonated α-amino groups on each lysine residue. The length of the oligolysine peptide (i.e. the number of lysine residues) is selected to be appropriate to the size and shape of the functional moiety 122, that is to be sufficient to provide an adequate shield to inhibit access to the active site of the functional moiety 122.

Without wishing to be bound by theory, it is believed that the positively charged lysine residues of the oligolysine peptides form electrostatic interactions with the peptide chains of the nanobody (functional moiety 122), thereby allowing the oligolysine peptides of each switchable molecule 121A, 121B, 121C . . . 121Z to fold around the nanobody (functional moiety 122) to inhibit access, for example, via steric hindrance. Access to the nanobody (functional moiety 122) may be sufficiently inhibited even when the oligolysines are only partially folded around the nanobody (functional moiety 122).

Upon application of a negative potential to the conductive layer of gold of the surface 120, the positively charged oligolysine chains are attracted towards the negatively charged conductive layer of gold of the surface 120. This causes the oligolysine chains (switchable molecule 121A, 121B, 121C . . . 121Z) to undergo a conformational change to unfold from around the nanobody (functional moiety 122). Without wishing to be bound by theory, it is believed that the negative potential provides sufficient energy to overcome any electrostatic interactions between the oligolysine peptides and the nanobody. The switchable molecules 121A, 121B, 121C . . . 121Z are thus provided in the stimulated state 200B, in which access to the functional moiety 122 (or at least one of the active or binding site thereof) is permitted. The switchable molecules 121A, 121B, 121C . . . , 121Z cease to conceal or inhibit access to the functional moiety 122.

This process may be reversible; reversing the stimulus applied to the system, for example the potential applied to the electrically responsive surface (i.e. removing the electrical potential) may transition the switchable molecule 121 from the stimulated state 200B back to the equilibrium state 200A.

In an embodiment, the substrate-bound switchable system may be immersed in a medium containing the target analyte 125.

In the stimulated state 200B, the target analyte 125 has access to, and may therefore bind to the functional moiety 122 to result in the analyte-bound state 200C, the response of which may be measured to record the presence of the target analyte 125 in solution, or to quantify the concentration of target analyte 125 in the solution.

Figure 8A:
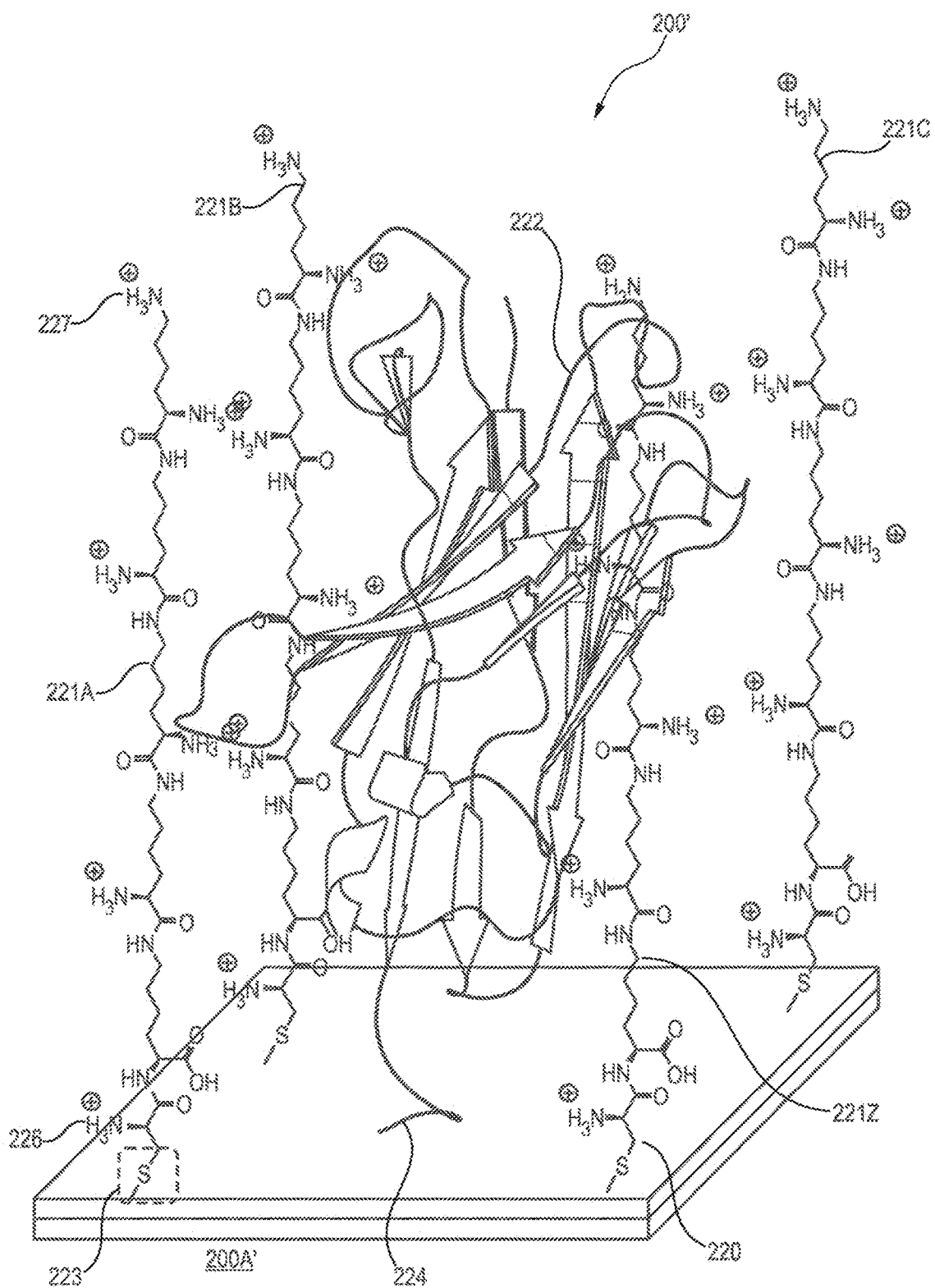
FIG. 8A is a schematic chemical structure of a first embodiment of the switchable molecule.

Referring now to FIG. 8A there is shown a schematic chemical structure of a substrate-bound switchable system 200' in its equilibrium state 200A' in which the stimulus is off. The substrate-bound switchable system 200' comprises four switchable molecules 221A, 221B, 221C, 221Z and a functional moiety 222, and a substrate 220. Each switchable molecule 221A, 221B, 221C, 221Z comprises an anchoring group 223, a proximal end 226, and a distal end 227 (shown for switchable molecule 221A only). Each functional moiety 222 comprises a connecting moiety 224.

In this embodiment, the substrate 220 comprises a conductive layer of gold. Each switchable molecule 221A, 221B, 221C, 221Z comprises an oligolysine peptide chain, each oligolysine peptide chain comprising five amino acids bonded in a linear arrangement.

The anchoring group 223 (shown for switchable molecule 221A only) connects each switchable molecule 221A, 221B, 221C, 221Z to the substrate 220. In this embodiment, the anchoring group 223 comprises a thiol group at the proximal end 226 of the oligolysine peptide chain of the switchable molecule 221A, which reacts to form a sulphur-gold bond with the layer of conductive gold of the substrate 220.

The functional moiety 222 comprises a nanobody. The nanobody may be Vascular Cell Adhesion Molecule-1 (NbVCAM1), which is an atherosclerotic biomarker, but other nanobodies may also be used in other embodiments of the invention.

The connecting moiety 224 connects the functional moiety 222 the substrate 220. In this embodiment, connecting moiety 224 of the functional moiety 222 comprises a sulphur-gold bond, wherein the functional moiety 222 comprises a thiol group that reacts with the layer of conductive gold of the substrate 220.

At physiological pH, each oligolysine in the peptide chain of each switchable molecule 221A, 221B, 221C, 221Z is protonated to provide a peptide with plural positive charges.

Advantageously, the number of amino acids in the peptide chain may be varied depending upon the size and shape of the functional moiety. Moreover, the functionality of the peptide chain can be altered according to need.

Figure 8B:
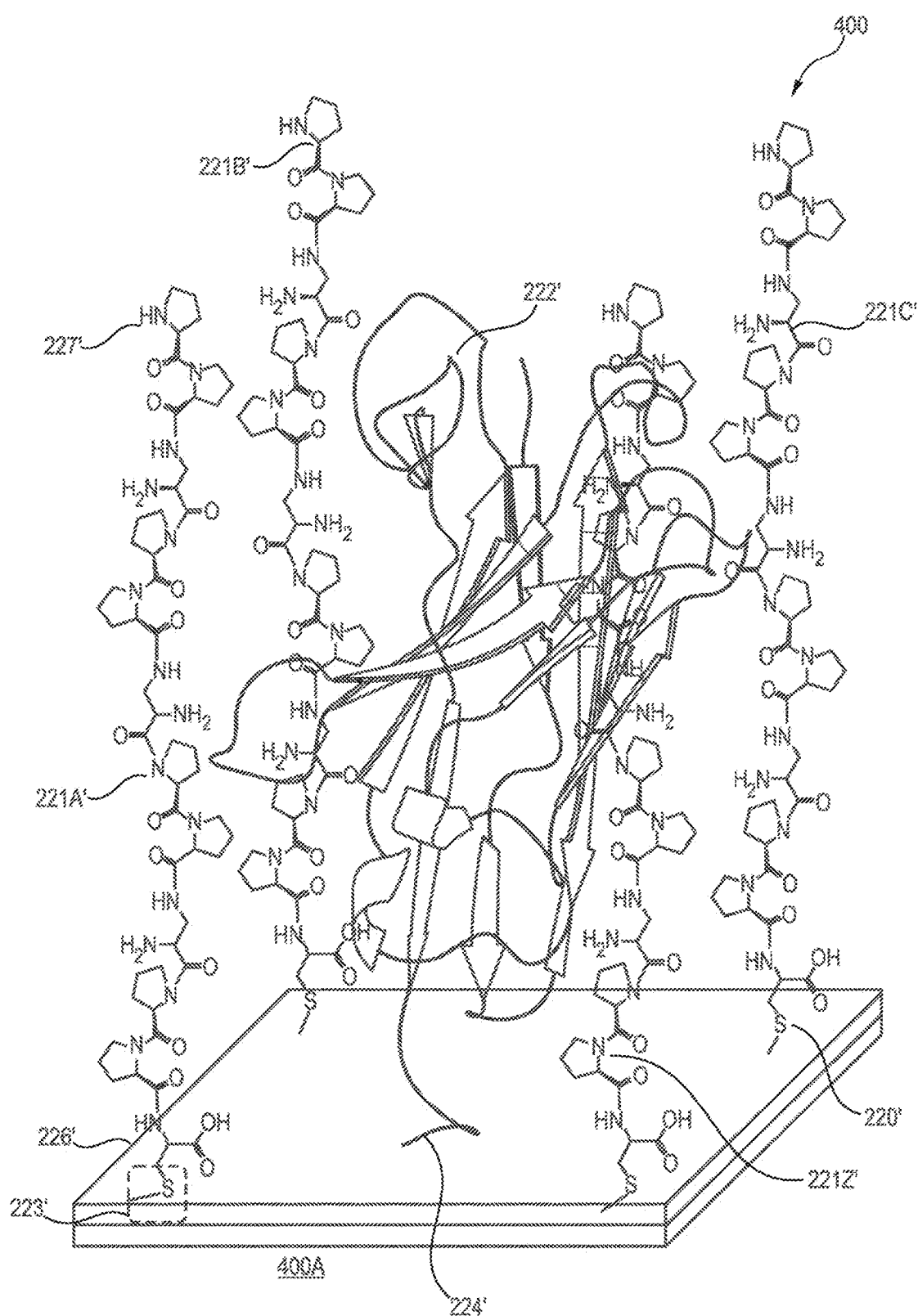
FIG. 8B is a schematic chemical structure of a second embodiment of the switchable molecule.

Referring now to FIG. 8B, there is shown a schematic chemical structure of a substrate-bound switchable system 400 in its equilibrium state 400A in which the stimulus is off. As this substrate-bound switchable system 400 similar to that previously described in FIG. 8A, the same numeric indicators will be used but distinguished by use of a prime ('). In this embodiment, each switchable molecule 221A', 221B', 221C', 221Z' comprises a peptide comprising two types of amino acid; proline and 2,3-diaminopropionic acid (DAP). The peptide chain is formed in a linear chain comprising eleven amino acids, and a further amino acid comprising the anchoring group 223' at the proximal end 226'. The peptide chain of the switchable molecule 221A' is formed from a repeating pattern of two proline monomers, and one DAP monomer. The distal end 227' comprises a proline monomer. The proximal end 226' comprises a proline monomer, which is bonded to an amino acid comprising the anchoring group 223', which comprises a thiol group. Each of the switchable molecule 221A', 221B', 221C', 221Z' comprise the structure described for 221A'.

The amino acid 2,4-diaminobutyric acid (DAB) may be used instead of DAP in this embodiment. Without wishing to be bound by theory, it is believed that provision of the DAP and/or DAB monomers in the peptide impart greater rigidity (in comparison to, for example, peptides comprising ornithine and/or lysine) to the switchable molecules 221A', 221B', 221C', 221Z', when in the equilibrium state 400A in which the stimulus is off. In this way, the rigidity of the peptide of the switchable molecule may be tuned.

Figure 8C:
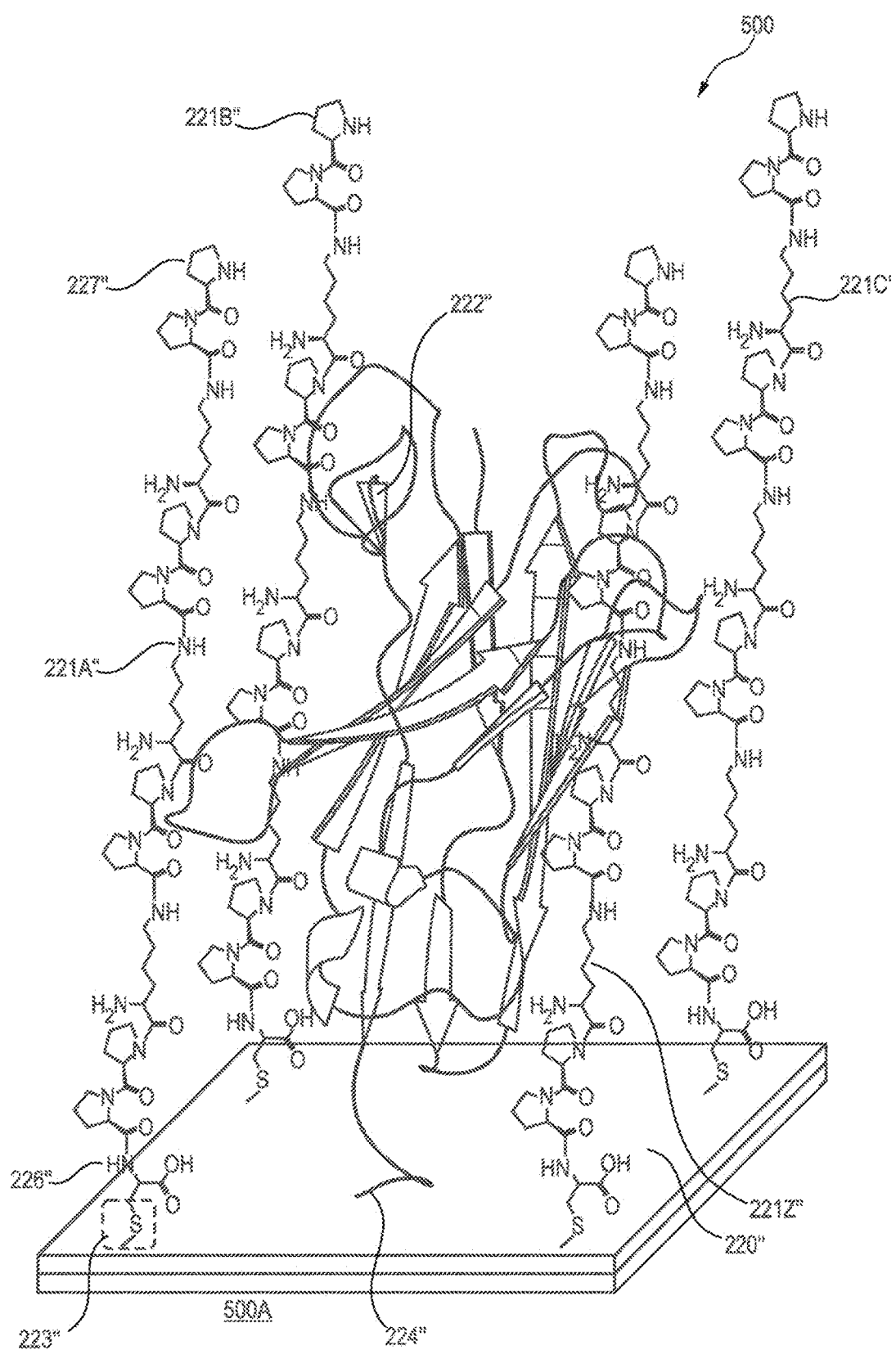
FIG. 8C is a schematic chemical structure of a third embodiment of the switchable molecule.

Referring now to FIG. 8C, there is shown a schematic chemical structure of a substrate-bound switchable system 500 in its equilibrium state 500A in which the stimulus is off. As this substrate-bound switchable system 500 is similar to that previously described in FIG. 8B, the same numeric indicators will be used but distinguished by use of an additional prime (").

In this embodiment, each switchable molecule 221A", 221B", 221C", 221Z" comprises a peptide comprising two types of amino acid; proline and lysine. The peptide chain is formed in a linear chain comprising eleven amino acids, and a further amino acid comprising the anchoring group 223" at the proximal end 226". The peptide chain of the switchable molecule 221A" is formed from a repeating pattern of two proline monomers, and one lysine monomer. The distal end 227" comprises a proline monomer. The proximal end 226" comprises a proline monomer, which is bonded to an amino acid comprising the anchoring group 223". Each of the switchable molecule 221A", 221B", 221C", 221Z" comprise the structure described for 221A".

Advantageously, the peptides of the switchable molecules described may be designed to suit the size and/or shape functionalised moiety. For example, the length of the peptide chain and/or the number of amino acid monomers, may be varied. Additionally, more than one type of amino acid may be used in the chain, for example, to obtain charges in specific parts of the peptide of the switchable molecule. In this way, a specific switchable molecule may be designed, which is suitable for a specific application, i.e. when using a particular functionalised moiety.

In FIGS. 8B and 8C, the amine groups of the switchable molecules 221A', 221B', 221C', 221Z', and 221A", 221B", 221C", 221Z" are deprotonated. However, in use, the substrate-bound switchable system 400, 500 is exposed to physiological pH and the amine groups are protonated to provide plural positive charges.

It is understood that the number of switchable molecules in a substrate-bound switchable system need not be limited to a ratio of four switchable molecules to one functional moiety. The ratio may be less than four switchable molecules to one functional moiety, for example, it may be a ratio of one, two or three switchable molecules to one functional moiety. Alternatively, the ratio may be greater than four switchable molecules to one functional moiety, for example, it may be a ratio of five, six, seven, eight, nine, ten or more switchable molecules to one functional moiety.

In alternative embodiments, the switchable molecules, e.g. 221A, 221B, 221C, and 221Z may comprise or be oligopeptides with negative charges. In this case, the stimulus is a negative potential Δv.

In some embodiments, short oligo(ethylene glycol) molecules (not shown) may be employed as lateral spacers to allow sufficient spatial freedom for synergistic molecular reorientation of the surface-bound switchable molecules and/or functional moieties.

Apart from having a positive effect on the switching efficiency, the short oligo(ethylene glycol) groups prevent non-specific interactions with the surface. Additionally, the short oligo(ethylene glycol) groups promote an 'upright' organisation of the peptide chains of the switchable molecules.

There is a broad range of nanobodies commercially-available for detecting different analytes with high specificity and affinity. However, their immobilization in a biosensor would typically rely in a random conjugation either using the carboxylic acid or amino groups available in the nanobody itself. This would lead to the immobilization of some nanobodies in a configuration where the binding sites would never be available for analyte binding. Thus, and in order to maximise the use of the nanobodies in the biosensor, we carry out a covalent and uniformly oriented coupling of the nanobody, thereby to maximise the available binding sites.

Figure 9:
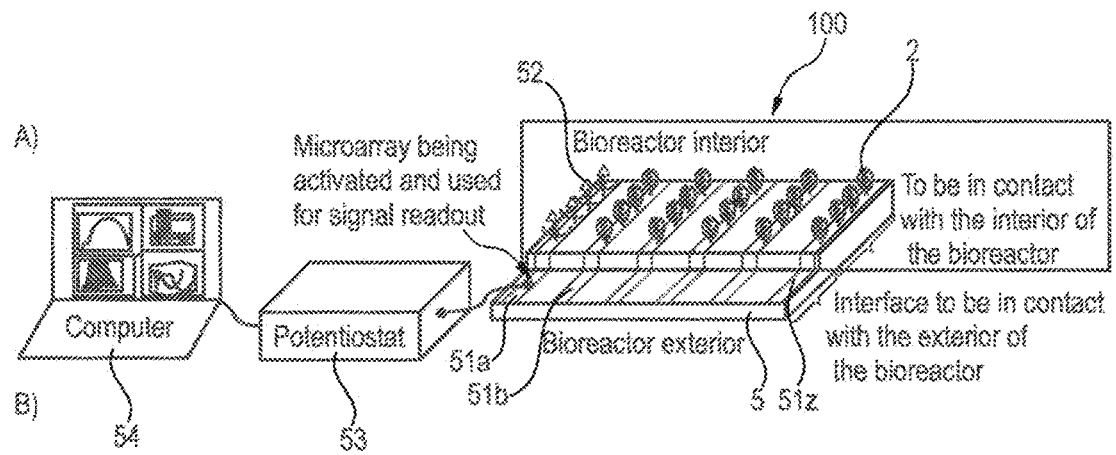
FIG. 9 is a schematic diagram of a biosensor according to the invention.

Referring now to FIG. 9, there is shown a bioreactor 100 according to the invention. The bioreactor 100 comprises an array of surface-bound switchable molecules 2 located on a conductive surface. In operation, the surface-bound switchable molecules 2 are exposed to physiological pH conditions, thereby causing protonation of the oligolysine double arms. The bioreactor 100 preferably comprises a gold micro-patterned glass chip 5 comprising a plurality of electrically switchable surfaces occupying discrete regions for the measurement of analyte. There is shown a potentiostat 53 for application of negative or positive potential across each of the electrically switchable surfaces 51a, 51b . . . 51z, and a computer 54 to monitor the biosensor 5 for detection of the analyte.

The gold micro-patterned glass chip 5 may be any size, for example, 1 cm×1 cm and each electrically switchable surfaces 51a, 51b . . . 51z, may be any size, for example, 2 microns×2 microns. Each electrically switchable surface 51a, 51b . . . 51z is independently electrically addressed allowing the use of one at a time for electrochemical-based activation and analyte binding measurements.

There may be several thousand electrically switchable surfaces 51a, 51b . . . 51z on each gold micro-patterned glass chip 5 allowing for hundreds of measurements per day over a period of, for example, three months or more. It is envisaged that a bioreactor will have multiple chips, each of the detection of a different analyte. Advantageously, this allows for low cost, long-term continuous and/or intermittent sampling of multiple analytes in a solution, for example, in a bioreactor.

The concentration of analyte 52 may be detected and quantified by known electrochemical based methods and techniques, for example, electrochemical impedance spectroscopy, which can measure quantities down to the zeptomole level.

A solution comprising an analyte is contacted with the interior of the bioreactor and a negative potential applied to the conductive surface, thereby causing the switchable molecules 2 to adopt an active state and allowing the analyte to bind to the functional moiety 22 (in this case the nanobody).

Figure 10:
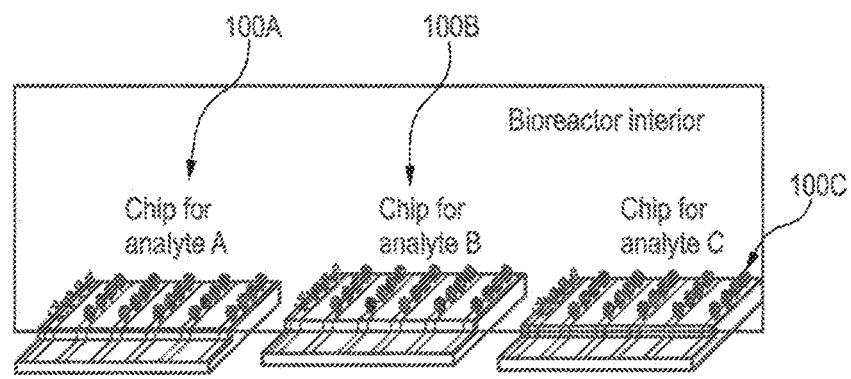
FIG. 10 shows a further biosensor of the invention.

FIG. 10 shows an embodiment whereby a complex mixture of analytes can be analysed by multiplexing bioreactors 100A, 100B, 100C (either in parallel or series). In this embodiment, each of the bioreactors 100A, 100B, 100C . . . 100n, comprise switchable molecules with a functional moiety arranged to bind to a different analyte. By exposing each of the bioreactors 100A, 100B, 100C to the solution to be analysed it is possible to determine the presence of plural analyte molecules.

Whilst the above has detailed oligolysine switchable molecules, which may be shielding portions, in an alternative embodiment, the switchable molecules may comprise oligoaspartate peptide chains, which have multiple negative charges along their length by virtue of the deprotonated carboxylate groups on each of the aspartate residues. In this case, a positive electrical potential may be applied to the conductive layer of gold to transition from the equilibrium state 2A, 200A, in which access to the functional moiety 122 is inhibited, to the stimulated state 26, 2006, in which access to the functional moiety 22, 122 is permitted.

The amino acid residues in the shielding portion of the switchable molecules need not be limited to lysine or aspartic acid. The oligoaspartate chains may be substituted with, for example, oligoglutamate chains. Alternatively, any other amino acid with a charged moiety may be selected for use in the invention. Additionally, the shielding portion of the switchable molecules need not be a peptide, and may be a different charged species such as a polyelectrolyte, for example poly(sodium styrene sulfonate) (PSS) or polyacrylic acid (PAA), or any other polymer chain possessing a carboxylic acid, amino, sulfonate, phosphate or any other charged group. The structure of the shielding portion of the switchable molecules may be modified to complement the structure of the functional moiety, and the intermolecular forces required for the shielding portion to fold around the functional moiety, to provide the steric hindrance required to inhibit access to the functional moiety.

In an alternative embodiment, the anchoring group 23A, 123 is a siloxane bond, which is formed by reaction of a silane with substrate 20, 120 comprising indium tin oxide (ITO). Advantageously, siloxanes are very stable and impart high thermal stability and chemical resistance to the stimuli-responsive surfaces of the present invention. Therefore, the functionality of the invention will be maintained in harsh conditions and also when a high potential is applied.

Accordingly, many different anchoring groups and/or connecting sites can be deployed, depending upon the nature of the substrate and the nature of the functional moiety. Advantageously, peptide engineering is sufficiently advanced to allow the various components of the switchable molecule to be configured as appropriate.

Figure 11:
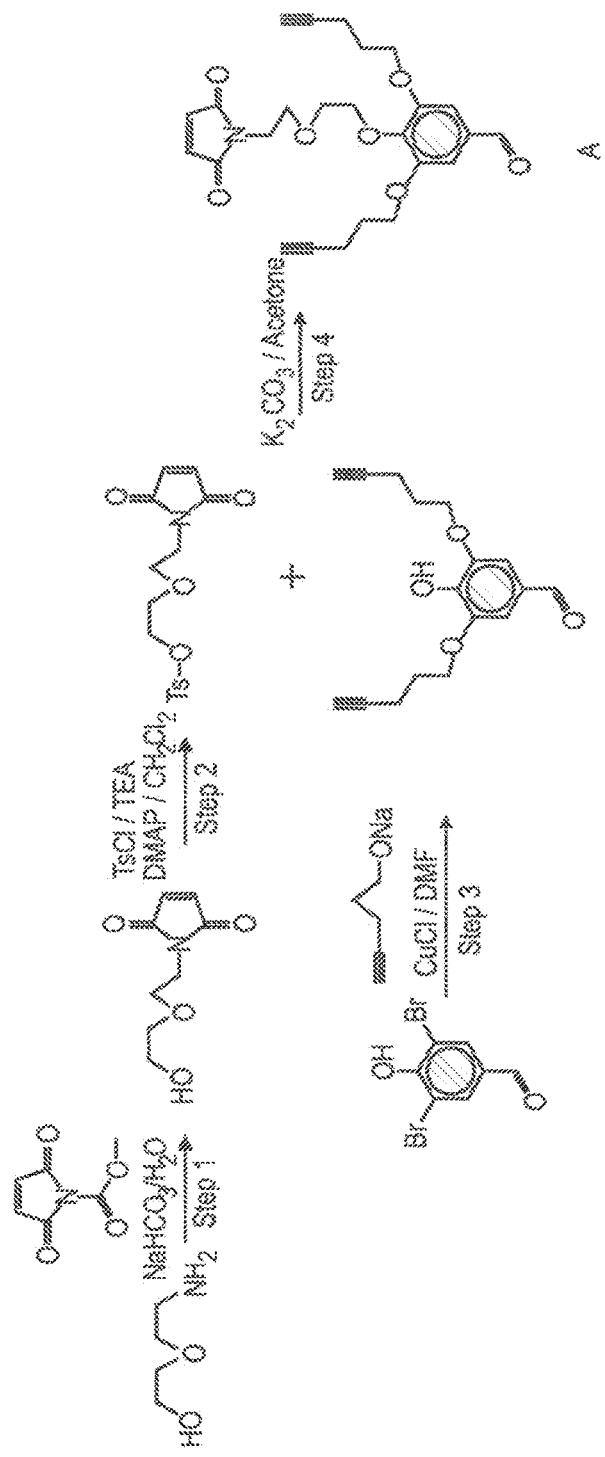
FIG. 11 shows a reaction scheme for forming a switchable molecule according to the invention.
Figure 12A:
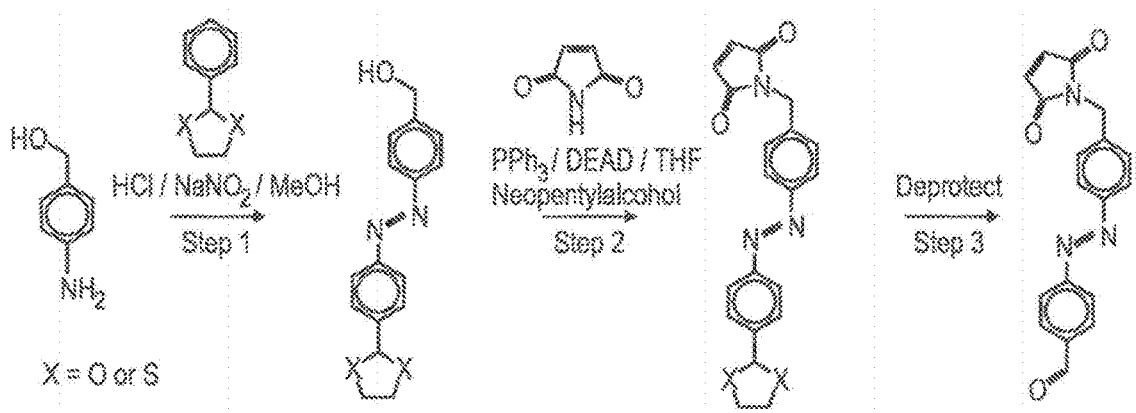
FIG. 12A shows a further reaction scheme for forming a further switchable molecule according to the invention.
Figure 12B:
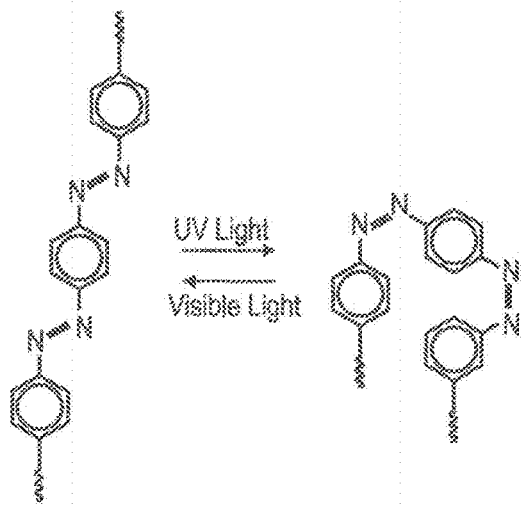
FIG. 12B shows a portion of a further embodiment of the switchable molecule.

Alternatively, it is possible to use a different approach, as indicated in FIGS. 11, 12A and 12B.

Referring now to FIG. 11, for the embodiment shown in FIG. 2, a benzaldehyde derivative A has been synthesised via the straightforward route shown in FIG. 11, which contains an aldehyde group for attachment to the surface, a maleimide group for attachment of the biomolecule and alkyne groups for attachment of the molecular arms. Compounds have been analysed by elemental analysis, NMR, and mass spectroscopies. Referring now to FIGS. 12A and 12B, light-switch molecular systems may also be used as switchable molecules that contain, for example, a photoresponsive azobenzene chromophore (which may be fabricated by the scheme shown in FIG. 12A) which serves as a vehicle for triggering changes in geometry by cis-trans photoisomerisation (FIG. 12B). The azo chromophore isomerises by illumination with UV light ($\lambda$=300-400 nm) from the stable trans form to the cis state, while reverse isomerisation can be triggered by irradiation with visible light ($\lambda$=425-500 nm) or by thermal relaxation. It is worth noting that the thermal cis-trans relaxation is very slow, taking up to 24 hours in the dark at room temperature. The isomerisation of this well-studied chromophore is accompanied by an appreciable shape change as the trans isomer adopts a more linear conformation than the cis isomer. In embodiments, the change in the molecular conformation of the azobenzene is employed to selectively expose (trans state) or conceal (cis state) the functional moiety upon photoactivation of the surface-bound biomolecule azobenzene components. Small changes in the conformation/orientation of the biomolecule by the azobenzene isomerisation can affect its binding activity.

Whilst many different species can be used as the functional moiety, the use of nanobodies as the functional moiety has a number of advantages. Nanobodies have high specificity and affinities towards the target analytes, in addition to being resistant to extreme pH, heat denaturation, proteolysis, solvents and detergents. Advantageously, this allows the biosensors embodied in FIGS. 9 and 10 to be cleaned and sterilised without affecting their future utility. More advantageously, this allows the biosensors of FIGS. 9 and 10 to be utilised in long-term continuous and/or intermittent sampling of bioreactors, where conditions may be complex. For example, the reaction may contain many different analytes in a complex reaction media, it may be a complex biological medium, or a high fouling medium. The high specificity and affinity shown towards the target analytes provides a very sensitive and accurate biosensor. Additionally, there is no need for sample manipulation or preparation, and more advantageously, there is no risk of contamination.

The present invention has several advantages over the prior art system. For example, the system exhibits an 'off' or equilibrium state, in which access to the functional moiety is inhibited, when no potential is applied. This is in contrast to the system of the prior art, in which a potential must be applied for the system to exhibit an 'off' or equilibrium state.

Additionally, the biorecognition component does not need to change conformation, nor change its spatial arrangement, to switch from the equilibrium state to the stimulated state. Only the shielding portion is required to change conformation. This allows greater switching efficiencies to be achieved in comparison to the prior art system.

The invention is not limited to the use of electricity as the stimulus. It is envisaged that other types of stimulus may be used. For example, the system may comprise switchable sensing components that respond to light, by for example cis/trans isomerisation or to temperature.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. For the avoidance of doubt, the terms "may", "and/or", "e.g.", "for example" and any similar term as used herein should be interpreted as non-limiting such that any feature so-described need not be present. Indeed, any combination of optional features is expressly envisaged without departing from the scope of the invention, whether or not these are expressly claimed. The applicant reserves the right to change any originally filed claim or file any new claim accordingly, including the right to amend any originally filed claim to depend from and/or incorporate any feature of any other claim although not originally claimed in that manner.

It will also be appreciated by those skilled in the art that any number of combinations of the aforementioned features and/or those shown in the appended drawings provide clear advantages over the prior art and are therefore within the scope of the invention described herein.

The invention claimed is:

1. A stimuli-responsive surface comprising a substrate on which is located plural switchable molecules which have a functional moiety associated therewith, wherein each of the switchable molecules comprises an anchoring moiety which anchors each of the switchable molecules to the substrate and the functional moiety comprises a connecting group which anchors the functional moiety to the substrate, wherein the plural switchable molecules and functional moiety are independently located on the substrate and wherein the substrate is electrically conductive or comprises an electrically conductive layer, such that each of the switchable molecules is configured to have a first equilibrium state in which access to the functional moiety is inhibited and a second stimulated state, in which access to the functional moiety is permitted by a conformational change in each of the switchable molecules upon application of an electrical potential to the substate, thereby exposing a bioactive molecular moiety of the functional moiety capable of binding an analyte.

2. A stimuli-responsive surface according to claim 1, wherein the substrate comprises a layer comprising a conductive ceramic layer.

3. A stimuli-responsive surface according to claim 1, wherein each of the switchable molecules comprises a shielding portion, the shielding portion being configured upon application of a stimulus to cause each of the switchable molecules to transition from the first equilibrium state to the second stimulated state.

4. A stimuli-responsive surface according to claim 3, wherein the shielding portion comprises at least one peptides associated with the functional moiety.

5. A stimuli-responsive surface according to claim 4, wherein the at least one peptide comprises one or more of lysines, aspartic acids, arginine, histidine or glutamic acid.

6. A stimuli-responsive surface according to claim 4, wherein each of the switchable molecules comprises a first peptide segment which provides a connecting portion and a second peptide segment which provides the shielding portion.

7. A stimuli-responsive surface according to claim 6, wherein the first peptide segment comprises or is a cyclic peptide.

8. A stimuli-responsive surface according to claim 7, wherein the second peptide segment is an arm or a side chain of or from the first peptide segment.

9. A stimuli-responsive surface according to claim 7, further comprising a third peptide segment which is an arm or a side chain of or from the first peptide segment.

10. A stimuli-responsive surface according to claim 9, wherein at least one of the second peptide segment and the third peptide segment comprise lysines, aspartic acids, arginine, histidine or glutamic acid.

11. A stimuli-responsive surface according to claim 1, wherein the functional moiety is selected from the group consisting of a single-domain antibody, a protein, a hormone, and a vitamin or another type of biomolecule or a small molecule.

12. A stimuli-responsive surface according to claim 1, wherein the anchoring moiety or an anchoring moiety group is selected from a thiol group to enable each of the switchable molecules to be anchored to a gold conductive layer or gold substrate or a silane group to enable each of the switchable molecules to be anchored to an ITO or a glass surface, to form a siloxane (Si—O) bond.

13. A stimuli-responsive surface according to claim 1, further comprising lateral spacer molecules.

14. A method of fabricating a stimuli-responsive surface, the method comprising step a) locating a functional moiety on an electrically conductive substrate with a connecting moiety, and step b) locating plural stimuli-responsive switchable molecules on the electrically conductive substrate with an anchoring group, the plural stimuli-responsive switchable molecules and the functional moiety being independently located on the electrically conductive substrate, the plural stimuli-responsive switchable molecules comprising at least one peptide and being configured to undergo a conformational change when an electrical potential is applied to the electrically conductive substrate to expose a bioactive molecular moiety of the functional moiety capable of binding an analyte.

15. A method for detecting an analyte, the method comprising applying an electrical potential across an electrically conductive surface to initiate a conformational change in plural switchable molecules from a first equilibrium state to a second active state thereby exposing a bioactive molecular moiety of a functional moiety capable of binding an analyte, the plural switchable molecules comprising at least one peptide and being located on and anchored to the electrically conductive surface by an anchoring moiety, the functional moiety being anchored to the electrically conductive surface by a connecting group, wherein the functional moiety is associated with the plural switchable molecules; wherein the plural switchable molecules and the functional moiety are independently located on a substrate.

16. A biosensor, the biosensor comprising a stimuli-responsive surface according to claim 1, and wherein the biosensor comprises means to apply an electric potential to the stimuli-responsive surface whereby each of the switchable molecules is able to transition from the first equilibrium state to the second stimulated state.

* * * * *